US011324555B2

(12) United States Patent
Maiorano et al.

(10) Patent No.: US 11,324,555 B2
(45) Date of Patent: May 10, 2022

(54) INSTRUMENT PORT INCLUDING OPTICAL BULB SECURED TO PORT BODY

(71) Applicant: The Children's Medical Center Corporation, Boston, MA (US)

(72) Inventors: Anthony Maiorano, Waltham, MA (US); Jeffrey C. Cerier, Franklin, MA (US)

(73) Assignee: The Children's Medical Center Corporation, Boston, MA (US)

( * ) Notice: Subject to any disclaimer, the term of this patent is extended or adjusted under 35 U.S.C. 154(b) by 1006 days.

(21) Appl. No.: 15/916,667

(22) Filed: Mar. 9, 2018

(65) Prior Publication Data

US 2019/0274761 A1 Sep. 12, 2019

(51) Int. Cl.
*A61B 34/20* (2016.01)
*A61B 90/30* (2016.01)
(Continued)

(52) U.S. Cl.
CPC ............ *A61B 34/20* (2016.02); *A61B 1/0008* (2013.01); *A61B 1/00137* (2013.01); *A61B 1/018* (2013.01); *A61B 17/3417* (2013.01); *A61B 17/3421* (2013.01); *A61B 90/30* (2016.02); *A61B 90/361* (2016.02);
(Continued)

(58) Field of Classification Search
CPC .............. A61B 1/00066; A61B 1/0008; A61B 1/00089; A61B 1/00096; A61B 1/00101; A61B 1/00105; A61B 1/00128; A61B 1/00137; A61B 1/0125; A61B 1/018;
(Continued)

(56) References Cited

U.S. PATENT DOCUMENTS 2,243,992 A 6/1941 Wappler
2,487,502 A * 11/1949 Willinsky ............ A61B 18/149
606/46
(Continued)

FOREIGN PATENT DOCUMENTS

EP 1426072 A1 6/2004
EP 2433551 A1 3/2012
(Continued)

OTHER PUBLICATIONS

International Search Report & Written Opinion, PCT/US17/17446, dated May 5, 2017, 16 pages (Year: 2017).*
(Continued)

*Primary Examiner* — Michael J Carey
*Assistant Examiner* — Stephen Floyd London
(74) *Attorney, Agent, or Firm* — Fish & Richardson P.C.

(57) ABSTRACT

An instrument port includes a port body, a bulb disposed at the distal end of the port body, a base body disposed at the proximal end of the port body, a hollow cylindrical body mechanically coupled to the base body, and a plurality of connecting rods disposed parallel to the port body. Each connecting rod includes a distal rod portion that is mechanically coupled to a respective distal-facing exterior surface of a bulb flange and a proximal rod portion that is mechanically coupled to a respective proximal-facing surface of the base body. A spring applies a spring force against the port body to press the port body into the bulb to mechanically secure the bulb to the base body.

20 Claims, 21 Drawing Sheets

(51) Int. Cl.
*A61B 90/00* (2016.01)
*A61B 17/34* (2006.01)
*A61B 1/00* (2006.01)
*A61B 1/018* (2006.01)
*A61B 18/00* (2006.01)

(52) U.S. Cl.
CPC ....... *A61B 1/00096* (2013.01); *A61B 1/00142* (2013.01); *A61B 2018/00982* (2013.01)

(58) Field of Classification Search
CPC .......... A61M 25/0069; A61M 39/1055; A61M 2039/1033; A61M 2039/1038
See application file for complete search history.

(56) References Cited

U.S. PATENT DOCUMENTS

| | | | |
|---|---|---|---|
| 2,767,705 | A | 10/1956 | Moore |
| 4,201,199 | A | 5/1980 | Smith |
| 4,233,982 | A | 11/1980 | Bauer et al. |
| 4,436,087 | A | 3/1984 | Ouchi |
| 4,503,843 | A * | 3/1985 | Boebel .................. A61B 1/303 600/114 |
| 4,535,773 | A | 8/1985 | Yoon |
| 5,025,778 | A | 6/1991 | Silverstein et al. |
| 5,217,001 | A | 6/1993 | Nakao et al. |
| 5,261,391 | A * | 11/1993 | Inoue .................... A61B 1/018 600/139 |
| 5,441,503 | A | 8/1995 | Considine et al. |
| 5,449,357 | A | 9/1995 | Zinnanti |
| 5,454,807 | A | 10/1995 | Lennox et al. |
| 5,632,782 | A | 5/1997 | Carlough |
| 5,660,175 | A | 8/1997 | Dayal |
| 5,797,960 | A | 8/1998 | Stevens et al. |
| 5,842,971 | A | 12/1998 | Yoon |
| 5,855,569 | A | 1/1999 | Komi |
| 5,876,329 | A * | 3/1999 | Harhen ............. A61B 1/00142 600/125 |
| 5,899,915 | A | 5/1999 | Saadat |
| 5,928,218 | A | 7/1999 | Gelbfish |
| 5,941,815 | A | 8/1999 | Chang |
| 6,033,426 | A | 3/2000 | Kaji |
| 6,129,713 | A | 10/2000 | Mangosong et al. |
| 6,178,346 | B1 | 1/2001 | Amundson et al. |
| 6,293,282 | B1 | 9/2001 | Lemelson |
| 6,309,345 | B1 | 10/2001 | Stelzer et al. |
| 6,315,714 | B1 | 11/2001 | Akiba |
| 6,503,192 | B1 | 1/2003 | Ouchi |
| 6,554,793 | B1 | 4/2003 | Pauker et al. |
| 6,641,562 | B1 | 11/2003 | Peterson |
| 6,689,085 | B1 | 2/2004 | Rubenstein et al. |
| 6,748,559 | B1 | 6/2004 | Pfister et al. |
| 6,749,559 | B1 | 6/2004 | Kraas et al. |
| 7,442,167 | B2 | 10/2008 | Dunki-Jacobs et al. |
| 7,537,562 | B2 | 5/2009 | Takano |
| 7,914,444 | B2 | 3/2011 | Moriyama et al. |
| 8,287,447 | B2 | 10/2012 | Gasche et al. |
| 8,394,015 | B2 | 3/2013 | Dibiasio et al. |
| 8,425,407 | B2 | 4/2013 | Sato et al. |
| 8,491,631 | B2 | 7/2013 | Del Nido et al. |
| 8,926,502 | B2 | 1/2015 | Levy et al. |
| 8,951,275 | B2 | 2/2015 | Cannon et al. |
| 9,451,875 | B2 | 9/2016 | Sigmon, Jr. et al. |
| 9,459,442 | B2 | 10/2016 | Miller |
| 9,709,795 | B2 | 7/2017 | Miller |
| 9,844,394 | B2 | 12/2017 | Dibiasio et al. |
| 2002/0026094 | A1 | 2/2002 | Roth |
| 2002/0068853 | A1 | 6/2002 | Adler |
| 2002/0111585 | A1 | 8/2002 | LaFontaine |
| 2004/0024414 | A1 | 2/2004 | Downing |
| 2004/0111019 | A1 | 6/2004 | Long |
| 2004/0116897 | A1 | 6/2004 | Aboul-Hosn |
| 2004/0193191 | A1 | 9/2004 | Starksen et al. |
| 2005/0197530 | A1 | 9/2005 | Wallace et al. |
| 2005/0234296 | A1 | 10/2005 | Saadat et al. |
| 2005/0234298 | A1 | 10/2005 | Kucklick et al. |
| 2006/0191975 | A1 * | 8/2006 | Adams ............... A61B 1/00087 227/180.1 |
| 2006/0264708 | A1 | 11/2006 | Horne |
| 2007/0066869 | A1 | 3/2007 | Hoffman |
| 2007/0197896 | A1 | 8/2007 | Moll et al. |
| 2008/0119695 | A1 * | 5/2008 | Ueno .................. G02B 23/2476 600/136 |
| 2008/0154288 | A1 * | 6/2008 | Belson ................. A61B 1/0055 606/150 |
| 2009/0048486 | A1 | 2/2009 | Surti |
| 2009/0275893 | A1 | 11/2009 | DiBiasio et al. |
| 2009/0318763 | A1 | 12/2009 | Koerner et al. |
| 2010/0038403 | A1 * | 2/2010 | D'Arcangelo ....... A61B 17/072 227/180.1 |
| 2010/0188493 | A1 * | 7/2010 | Kanzaki ............. A61B 1/00059 348/75 |
| 2010/0286475 | A1 * | 11/2010 | Robertson .......... A61B 1/00096 600/104 |
| 2011/0288372 | A1 | 11/2011 | Petersen |
| 2011/0295072 | A1 | 12/2011 | Boulais et al. |
| 2012/0100729 | A1 * | 4/2012 | Edidin ................. A61B 1/0057 439/38 |
| 2012/0193394 | A1 * | 8/2012 | Holcomb ........... A61B 17/0682 227/176.1 |
| 2012/0209074 | A1 | 8/2012 | Titus |
| 2012/0232342 | A1 | 9/2012 | Reydel |
| 2013/0245371 | A1 | 9/2013 | Mourlas et al. |
| 2013/0281779 | A1 | 10/2013 | Robertson |
| 2014/0213847 | A1 | 7/2014 | Green et al. |
| 2014/0213848 | A1 | 7/2014 | Moskowitz et al. |
| 2014/0221749 | A1 | 8/2014 | Grant |
| 2015/0065795 | A1 | 3/2015 | Titus |
| 2015/0313633 | A1 | 11/2015 | Gross et al. |
| 2016/0000463 | A1 | 1/2016 | DiBiasio et al. |
| 2016/0278626 | A1 * | 9/2016 | Cornhill ............. A61B 1/00154 |
| 2016/0345806 | A1 * | 12/2016 | Ishii .................... A61B 1/00071 |
| 2016/0367120 | A1 | 12/2016 | Dupont et al. |
| 2017/0231477 | A1 | 8/2017 | del Nido et al. |
| 2018/0279856 | A1 * | 10/2018 | Eisenkolb .......... A61B 1/00188 |

FOREIGN PATENT DOCUMENTS

| | | |
|---|---|---|
| WO | 1998024501 A1 | 6/1998 |
| WO | 1998040016 A2 | 9/1998 |
| WO | 20040112652 A2 | 12/2004 |
| WO | 2005051175 A2 | 6/2005 |
| WO | 2007081800 A2 | 7/2007 |
| WO | 2011047339 A2 | 4/2011 |
| WO | 2016205694 A1 | 12/2016 |
| WO | 2017139629 A1 | 8/2017 |

OTHER PUBLICATIONS

International Search Report & Written Opinion, PCT/US07/00270, dated Oct. 1, 2007.
Ataollahi et al., "Cardioscopic Tool-Delivery Instrument for Beating-Heart Surgery," IEEE ASME Transactions on Mechatronics, 21(1):1-1 (abstract), Jan. 2015 [retrieved on Apr. 15, 2019]. Retrieved from the internet: <URL:https://www.researchgate.net/publication/283309805_Cardioscopic_Tool-Delivery_Instrumentfor_Beating-Heart_Surgery>.
International Search Report and Written Opinion in International Application No. PCT/US2016/038147, dated Sep. 8, 2016.
Vasilyev et al.; "A Novel Cardioport for Beating-Heart Image-Guided Intracardiac Surgery" Children's Hospital Boston, Harvard Medical School, Boston, Massachusetts Institute of Technology, Cambridge, Massachusetts; International Society for Minimally Invasive Cardiothoracic Surgery (ISMICS); Jun. 3, 2009.
Vasilyev et al.; "Three-Dimensional Echo and Videocardioscopy-Guided Atrial Septal Defect Closure"; Annals of Thoracic Surgery; 2006; vol. 82; pp. 1322-1326.
Vasilyev et al.; "A novel cardioport for beating-heart, image-guided intracardiac surgery" The Journal of thoracic and Cardiovascular Surgery; vol. 142, No. 6; Dec. 2011; pp. 1545-1551.

(56) References Cited

OTHER PUBLICATIONS

Padala et al.; Transapical beating heart cardioscopy technique for off-pump visualization of heart valves; The Journal of thoracic and Cardiovascular Surgery; vol. 144, No. 1; 2012; pp. 231-234.
Shiose et al.; "Cardioscopy-guided surgery: Intracardiac mitral and tricuspid valve repair under direct visualization in the beating heart"; The Journal of thoracic and Cardiovascular Surgery; vol. 142, No. 1; 2011; pp. 199-202.
Uchida; "Recent Advances in Percutaneous Cardioscopy"; Curr Cardiovasc Imaging Rep; May 12, 2011; pp. 317-327.
Ahmed et al.; Initial clinical experience with a novel visualization and virtual electrode radiofrequency ablation catheter to treat atrial flutter; Heart Rhythm Society; 2011; pp. 361-367.
International Search Report and Written Opinion in International Application No. PCT/US17/17445, dated Jun. 6, 2017.
Ataollahi et al., "Cardioscopic Tool-Delivery Instrument for Beating-Heart Surgery," IEEE ASME Transactions on Mechatronics, vol. 21, No. 1, Feb. 2016, pp. 584-590.
European Patent Office, "Extended European Search Report", App. No. 17750861.1, dated Sep. 30, 2019, European Patent Office.
Extended European Search Report issued in EP07716358.2 dated Apr. 24, 2014.
P. Dupont; "Invention Disclosure—Cardioscopes"; May 21, 2016; 5pp.
Extended European Search Report in European Application No. 16812547.4, dated Feb. 21, 2019, 8 pages.
ISA, "International Search Report", PCT/US2018/021708, dated May 24, 2018.

\* cited by examiner

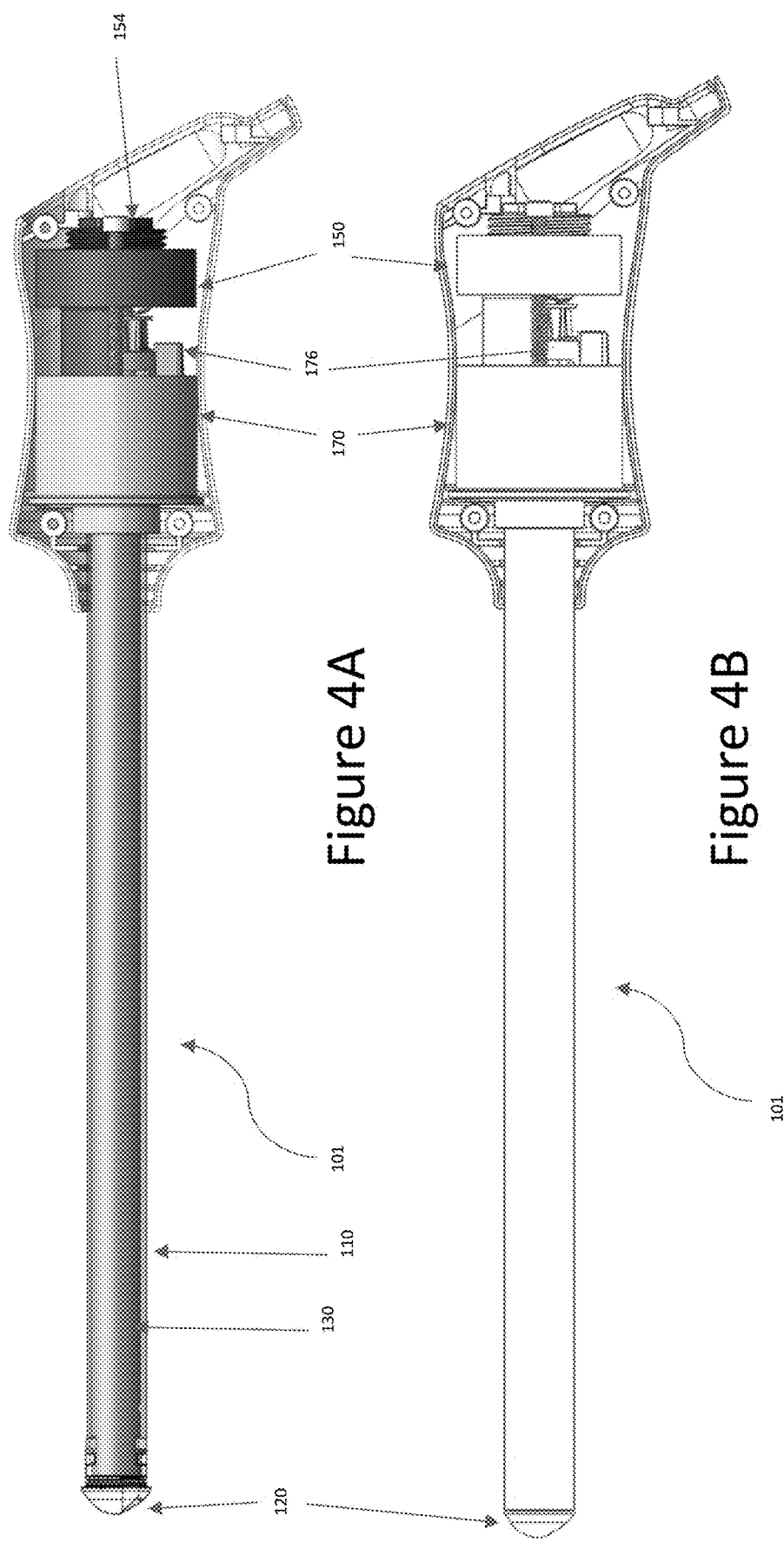

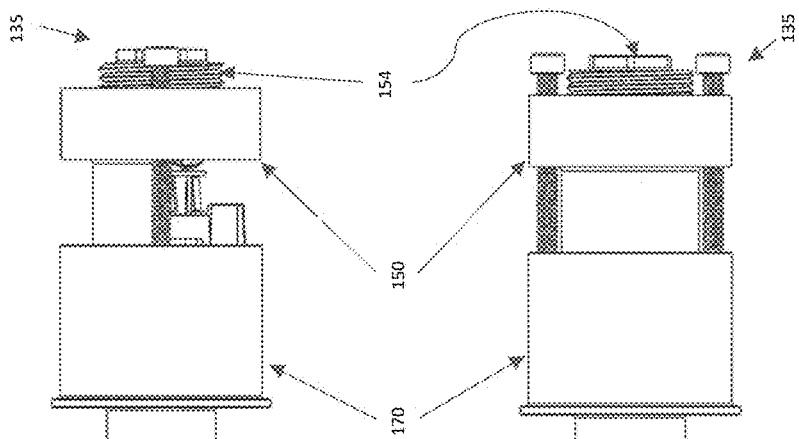
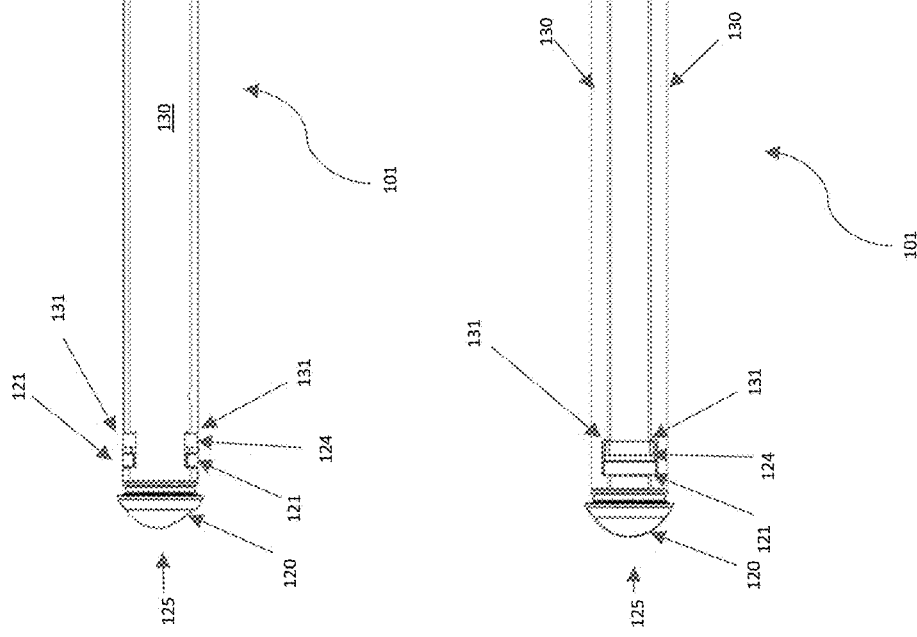
Figure 6A
Figure 6B

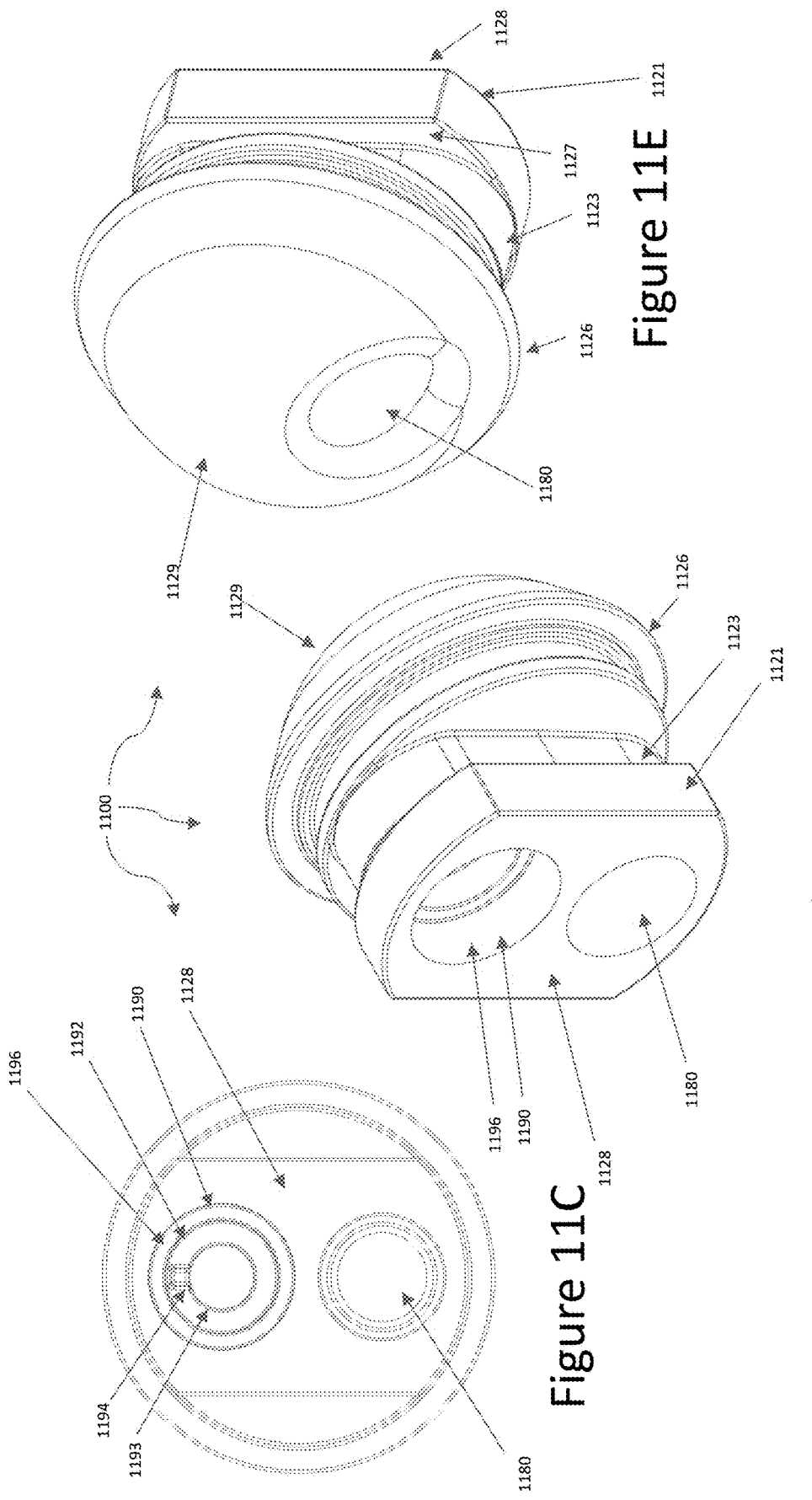

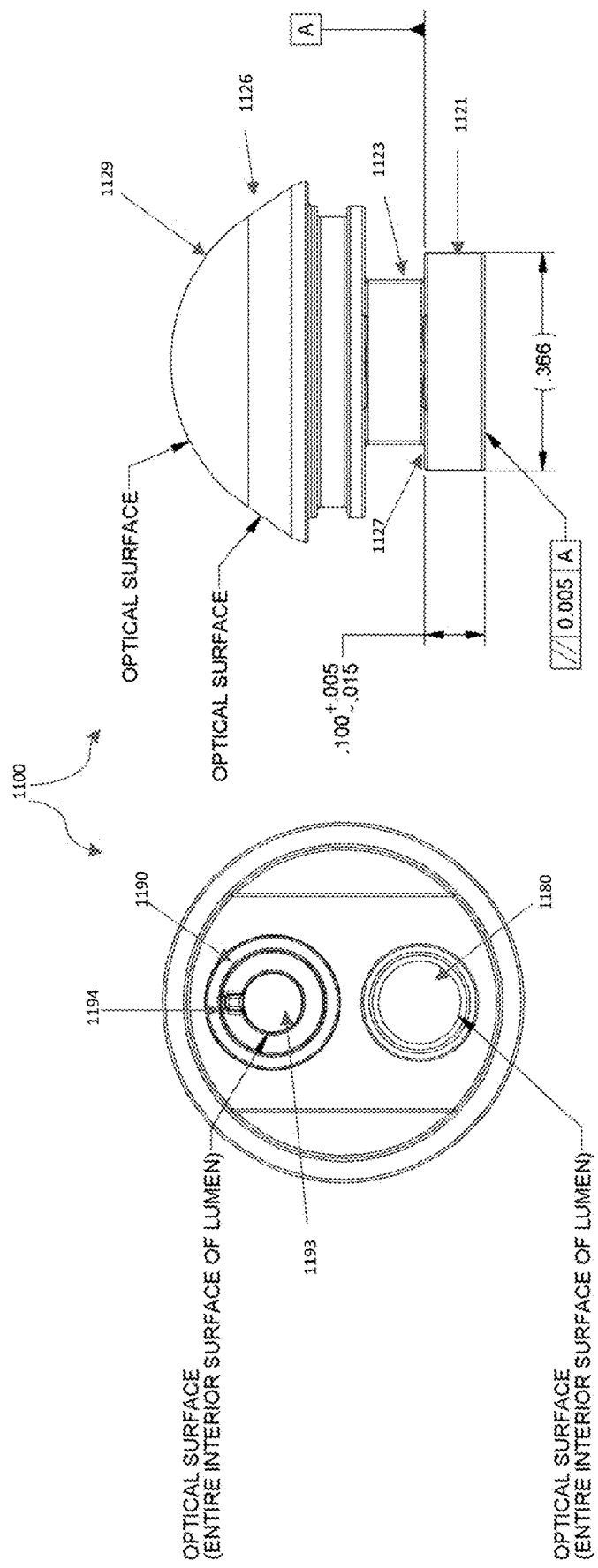

INSTRUMENT PORT INCLUDING OPTICAL BULB SECURED TO PORT BODY

STATEMENT REGARDING FEDERALLY-SPONSORED RESEARCH

This invention was made with U.S. government support under Grant No. 5R42HL132655, awarded by the Heart, Lung, and Blood Institute (NHLBI) of the National Institutes of Health (NIH). The U.S. government has certain rights in the invention.

TECHNICAL FIELD

This application relates generally to devices for minimally invasive image-guided surgery, such as cardiac surgery.

BACKGROUND

Instrument guides or ports can be used to guide the insertion of surgical instruments into a surgical site. Examples of procedures where such instruments ports or guides are used are beating-heart, minimally-invasive cardiac procedures to repair heart defects or to treat vascular heart disease. To position an instrument port at an appropriate location near the surgical site, current systems rely on either the operator's vision or a secondary optical system, such as an endoscope, that is inserted next to or into the instrument guide.

Positioning an instrument using the operator's vision is limited to procedures where the surgical site is within the operator's line-of-sight, and thus cannot be done for most internal surgical sites. One problem with secondary optical systems is that they require a separate imaging channel in the instrument guide to receive the optical system (e.g., an endoscope). This causes the instrument guide to be larger in diameter and more expensive in order to accommodate the separate imaging channel. When the secondary optical system is located next to the instrument guide, it is exposed to the body fluids (e.g., blood) near the surgical site which limits the clarity, field of view, and/or depth of view of the secondary optical systems. When the secondary optical system contacts body fluids, it increases the risk of infection. This risk is compounded each time that the secondary optical system is introduced to the surgical site.

Current surgical imaging solutions are unable to function effectively in an environment containing body fluids or other biological or surgical debris, contaminants or obstructions. Such fluids and contaminants are generally not optically transparent and have other mechanical and optical characteristics that degrade the functioning of imaging systems during surgery, e.g., in the presence of blood at the aperture of the imaging system, lens or other optical components. This makes the imaging system useless or ineffective in such environments.

Another problem with existing instrument guides is they rely on an adhesive to attach the optical bulb, containing the optical system, to the proximal portion of the instrument guide. However, the adhesive can fail or partially fail during use, often when the surgeon applies a large external force on the instrument guide. This can affect the position of the optical bulb, can introduce contaminants into the surgical site, and can cause the imaging system to fail.

It would be desirable to overcome one or more of these deficiencies.

SUMMARY

The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Other objects, advantages and novel features of the disclosure will be set forth in the following detailed description of the disclosure when considered in conjunction with the drawings.

An aspect of the invention is directed to an instrument port for introducing a surgical instrument into a surgical site inside a body of a patient, the instrument port comprising: a port body having a port body interior lumen extending from a proximal end to a distal end of the port body; a bulb disposed at the distal end of the port body, the bulb comprising a bulb connection point, such as a flange, at a proximal end of the bulb, the bulb further comprising a bulb channel extending from a proximal end to a distal end of the bulb, the bulb channel aligned with the port body interior lumen to form an instrument channel to receive the instrument; a base body disposed at the proximal end of the port body, said base body having an aperture extending from a proximal end to a distal end thereof, wherein internal threads are defined in the proximal end of the base body, the proximal end of the base body defining a proximal portion of said aperture; a hollow cylindrical body having external threads that mate with the internal threads of the base body, the hollow cylindrical body having a hollow cylindrical body channel extending from a proximal end to a distal end of the hollow cylindrical body, the hollow cylindrical body channel aligned with the instrument channel, wherein the distal end of the hollow cylindrical body is mechanically coupled to the proximal end of the base body; a plurality of connecting rods disposed parallel to the port body, each connecting rod comprising a distal rod portion that is mechanically coupled to a respective distal-facing exterior surface of the bulb flange, each said connecting rod further comprising a proximal rod portion that is mechanically coupled to a respective proximal-facing surface of the base body; and a spring disposed between the distal end of the hollow cylindrical body and the proximal end of the port body, wherein a compression of the spring causes the spring to generate a first spring mechanical force in the proximal direction and a second spring mechanical force in the distal direction, the first and second spring mechanical forces mechanically pressing the port body against the bulb.

In one or more embodiments, a position of the hollow cylindrical body with respect to the base body corresponds to the compression of the spring. In one or more embodiments, moving the position of the hollow cylindrical body in the distal direction increases a magnitude of the first and second spring mechanical forces. In one or more embodiments, moving the position of the hollow cylindrical body in the proximal direction decreases the magnitude of the first and second spring mechanical forces. In one or more embodiments, the first and second spring mechanical forces compress the port body and the bulb.

In one or more embodiments, the instrument port further comprises a compressible gasket disposed between the proximal end of the bulb and the distal end of the port body. In one or more embodiments, the second spring force pushes the distal end of the port body against the compressible gasket and the bulb to form a fluid-tight seal. In one or more embodiments, the compressible gasket includes a gasket hole, the gasket hole aligned with the bulb channel and the port body interior lumen.

In one or more embodiments, the bulb comprises an imaging system, said imaging system comprising an illumination source and a camera, said camera configured to capture images of the surgical site. In one or more embodiments, the port body comprises a second interior lumen, said second interior lumen comprising electrical conduits that are electrically connected to the imaging system. In one or more embodiments, the port body has a generally cylindrical shape. In one or more embodiments, the hollow cylindrical body comprises, on the proximal end thereof, one or more pairs of raised surfaces disposed on opposing sides of the hollow cylindrical body channel, said raised surfaces configured to allow the hollow cylindrical body to be rotated about a longitudinal axis that passes through said hollow cylindrical body channel.

In one or more embodiments, the instrument port further comprises a housing surrounding the base body and a proximal portion of the port body, said housing comprising a grip by which a surgeon is able to hold and manipulate the instrument port from outside the patient's body. In one or more embodiments, the instrument port further comprises a sleeve extending from the housing to the distal end of the port body, said sleeve comprising a tube of generally cylindrical shape and being disposed outside and enclosing the port body and the connecting rods.

In one or more embodiments, the distal rod portion includes a notch that engages the distal-facing exterior surface of the bulb flange. In one or more embodiments, the proximal rod portion includes a notch that engages the proximal-facing surface of the base body. In one or more embodiments, the connecting rods comprise aluminum.

BRIEF DESCRIPTION OF THE DRAWINGS

For a fuller understanding of the nature and advantages of certain aspects of the invention, reference is made to the following detailed description of preferred embodiments and in connection with the accompanying drawings, in which:

FIGS. 4A and 4B are side views.

FIGS. 6A and 6B are simplified side and top views, respectively, of the instrument port disclosed herein, according to one or more embodiments;

FIGS. 11A, 11B, 11C, 11D and 11E are side, front (distal), rear (proximal), rear perspective and front perspective views, respectively, of a bulb comprising a distal portion of the instrument port disclosed herein, according to one or more embodiments;

FIG. 12 is a rear (proximal) view of a bulb comprising a distal portion of the instrument port disclosed herein, according to one or more embodiments, with certain optical features shown; and FIG. 13 is a side view of a bulb comprising a distal portion of the instrument port disclosed herein, according to one or more embodiments, with exemplary dimensions and certain optical and other features shown.

DETAILED DESCRIPTION

An instrument port includes a plurality of connecting rods that extend from a respective proximal-facing surface of a base body to a respective distal-facing surface of a bulb flange, which is coupled to or a portion of an optical bulb. A proximal portion of each connecting rod is mechanically coupled to the respective proximal-facing surface of the base body, and a distal portion of each connecting rod is mechanically coupled to the respective distal-facing surface of the bulb flange, or other mechanical coupling as would be appreciated by those skilled in the art.

A spring is disposed between the proximal end of the port body and a distal end of a base body. A cylindrical hollow body or end cap can be inserted into an aperture defined in the base body. The position of the cylindrical hollow body or end cap corresponds to a magnitude of compression of the spring, which provides a force in a distal direction to secure the optical bulb to the port body by pressing the port body against the bulb, which is held in place by the connecting rods. The position of the cylindrical hollow body or end cap can be adjusted by rotating external threads on the cylindrical hollow body or end cap with respect to internal threads on the wall of the aperture of the base body.

Figure 1A:
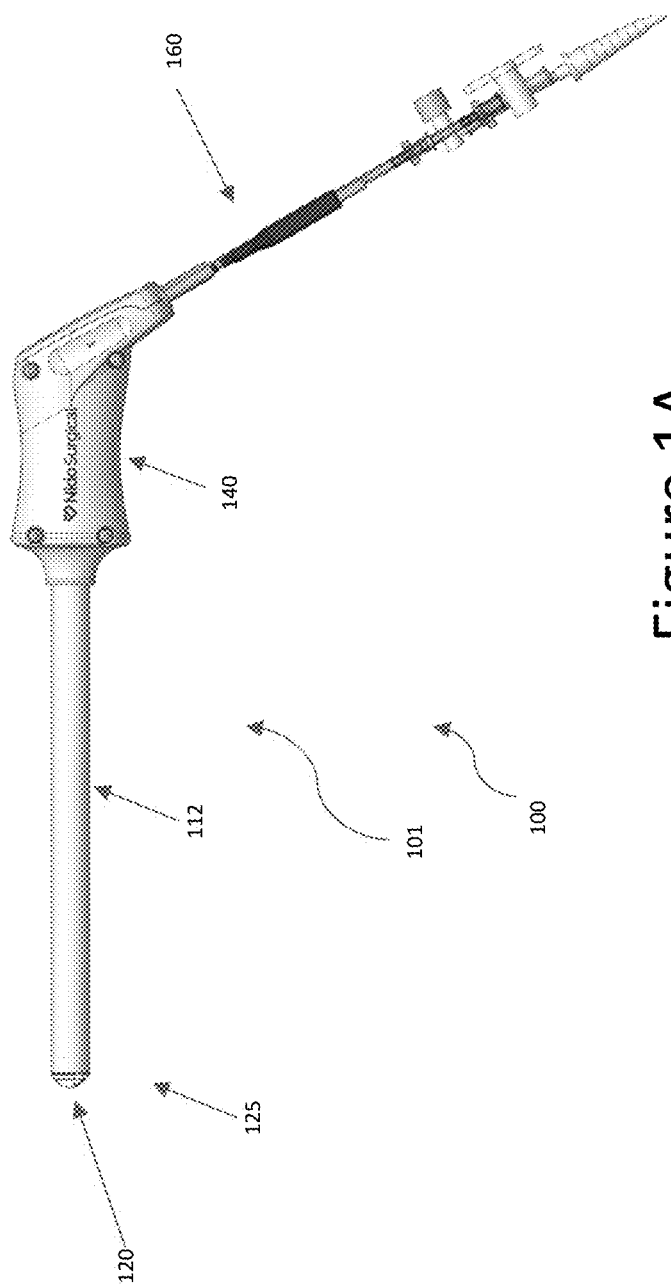
FIGS. 1A and 1B are side views.
Figure 1B:
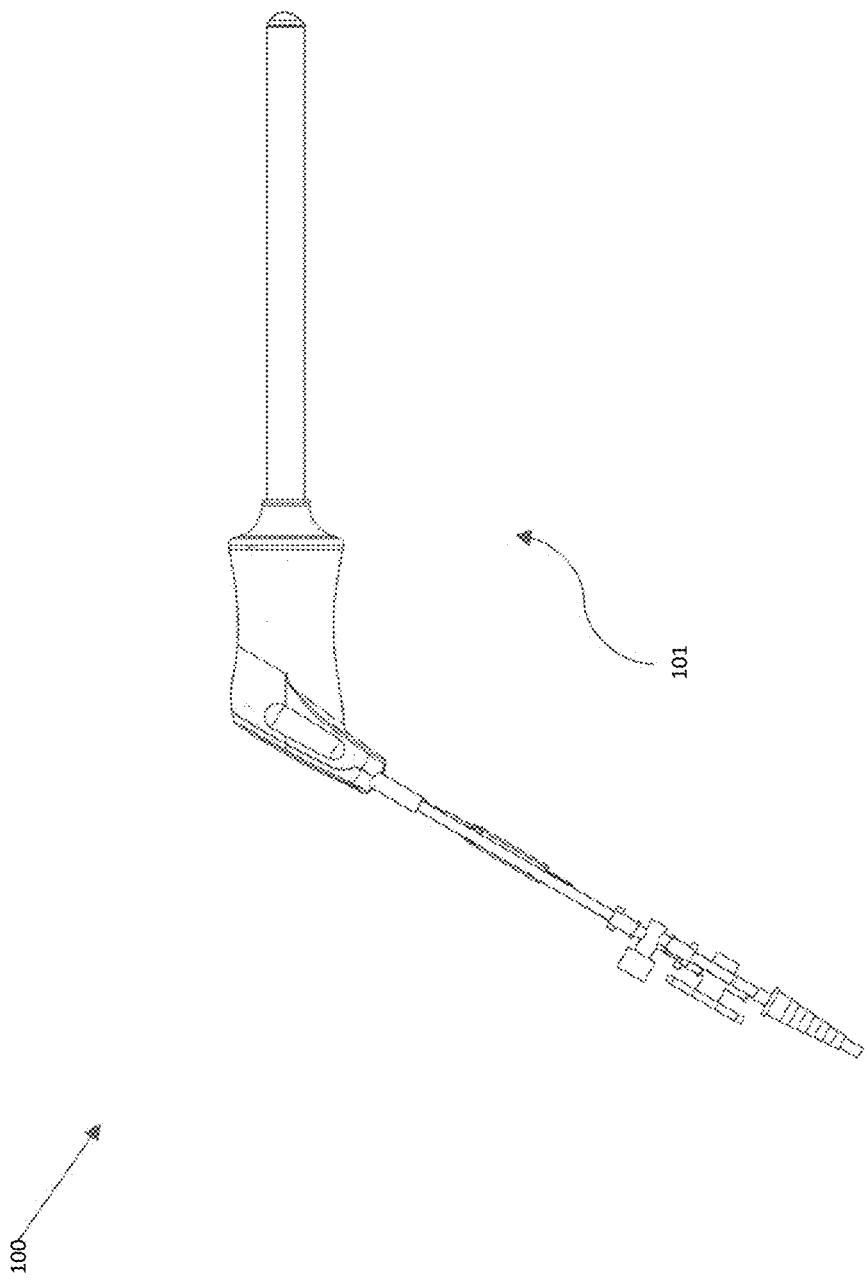
Figure 1C:
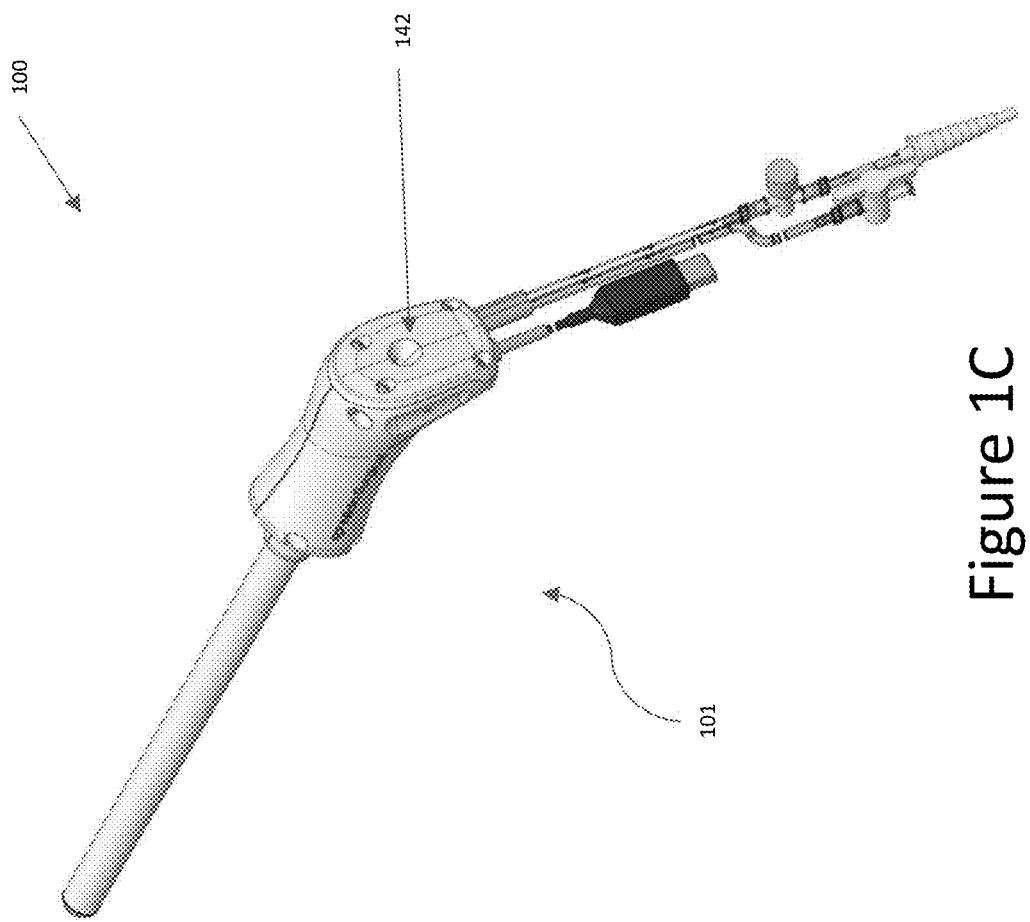
FIG. 1C is a perspective view, of a surgical apparatus including the instrument port disclosed herein, according to one or more embodiments.

FIGS. 1A, 1B and 1C illustrate an exemplary surgical apparatus 100 comprising instrument port 101 and fluid and electrical lines 160, with FIGS. 1A and 1B being side planar views and FIG. 1C being a perspective view. The instrument port 101 comprises bulb 120 at its distal end 125, a port body at least partially contained within sleeve 112, and other components contained within housing 140, which may be used by the surgeon as a handle or grip to manipulate and guide the apparatus 100 from outside the patient's body. The proximal face of housing 140 has an opening 142 for an instrument channel that extends to the distal end 125 of the instrument port 101 for introducing or guiding the surgical instrument into a surgical site inside the patient's body while being manipulated from outside the patient's body. The underside of housing 140 has connections to fluid and electrical lines 160, the latter for use in powering and/or receiving data from an imaging system that can be disposed in bulb 120. Housing 140 can surround a base body (as described herein) and a proximal portion of the port body. The sleeve 112 extends from the housing 140 to a distal end of the port body. The sleeve 112 includes an elongated tube that is disposed outside of and encloses at least a portion of port body and the connecting rods (as described herein).

Figure 2:
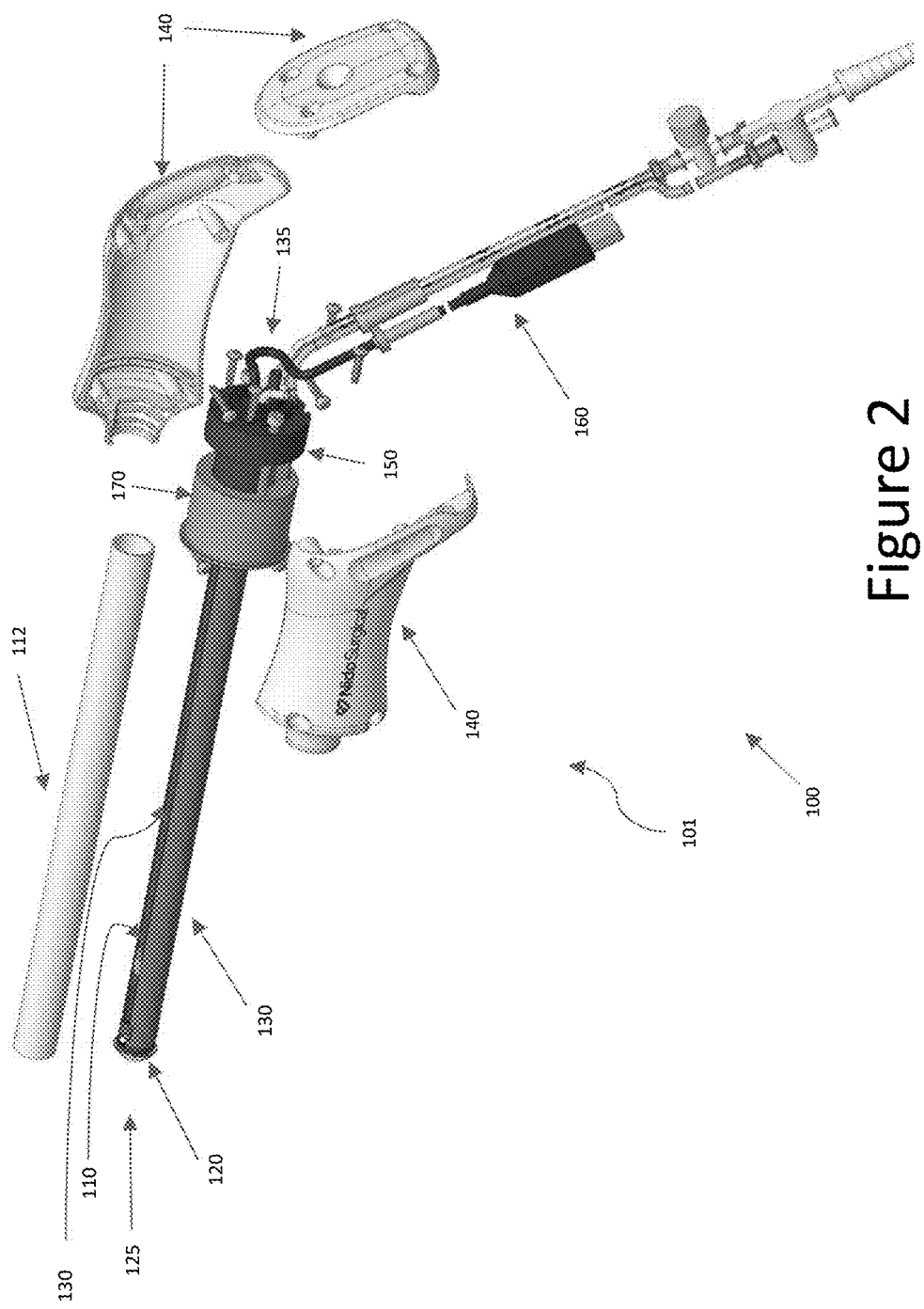
FIG. 2 is an exploded perspective view of the apparatus of FIGS. 1A and 1B, according to one or more embodiments.

FIG. 2 illustrates surgical apparatus 100 in a partly exploded perspective view. In this view, sleeve 112 and housing 140 are separated from the remainder of the instrument port 101, allowing interior parts to be seen. When the apparatus 100 is assembled, sleeve 112 encloses connecting rods 130 and port body 110, protecting these parts of the apparatus 100, and presenting a smooth exterior surface to bodily tissues with which the apparatus 100 may come in contact during surgical procedures. Inside of sleeve 112 is port body 110, with connecting rods 130 alongside it on each side. The connecting rods 130 and spring (not illustrated in FIG. 2) effect a secure mechanical connection between the port body 110 and bulb 120 at the distal end 125. The port body 110 is seated within base body 150 at proximal end 135, and the base body 150 and port body 110 are partly enclosed by collar 170. Electrical and fluidic connections 160 can be seen extending beyond base body 150 in the proximal direction.

Figure 3:
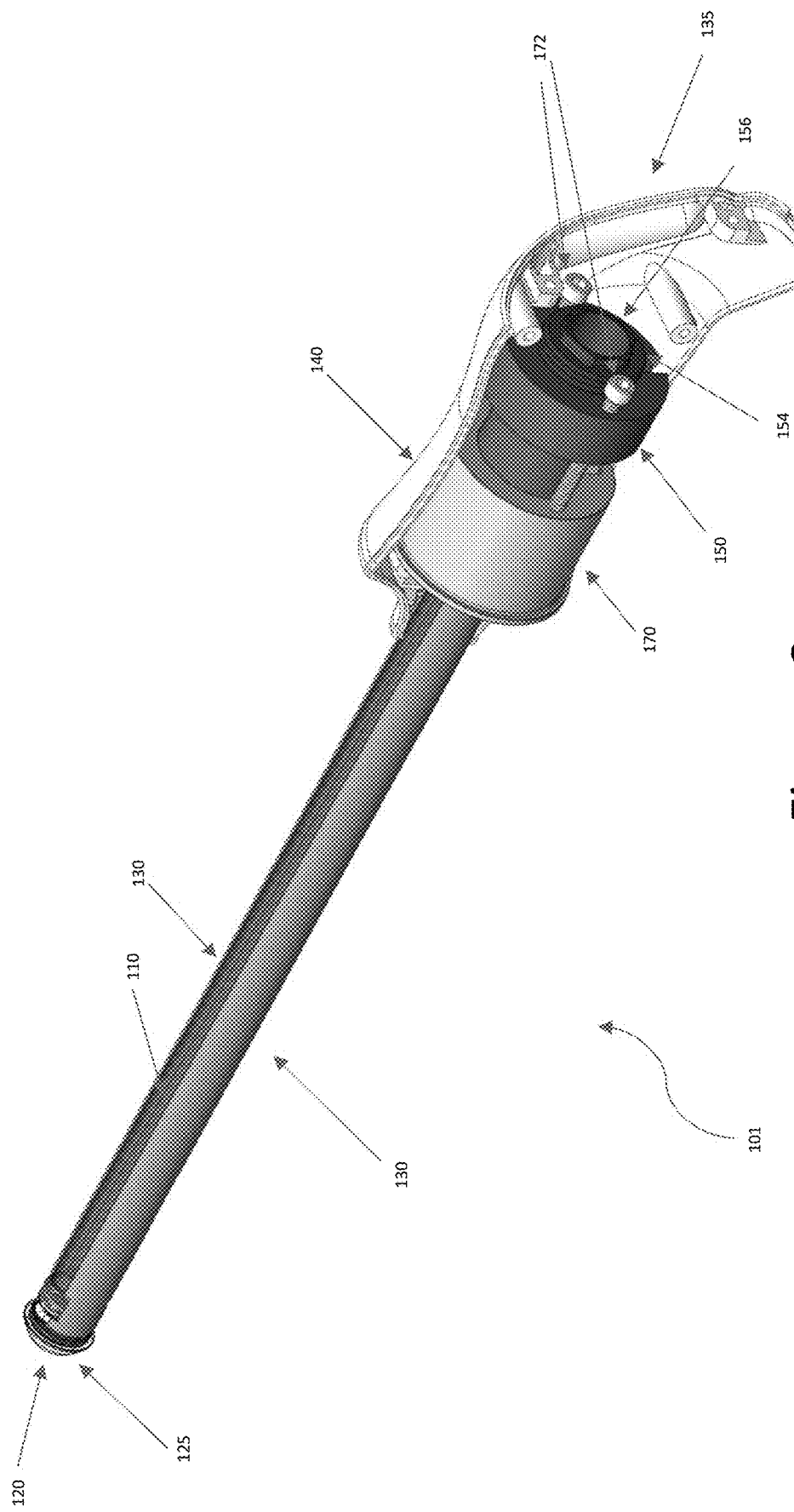
FIG. 3 is a cutaway perspective view.

FIG. 3 shows in perspective view the internal parts of instrument port 101 in more detail, focusing on the mechanical aspects of the assembly. Sleeve 112, part of housing 140 and connecting electrical and fluidic lines 160 from FIGS. 1-2 are not shown. As illustrated, rods 130 have a curved profile to conform to the tubular shape of the port body 110 and to minimize the overall profile of the instrument port 101, which can only need a small incision for insertion during surgery. Collar 170 fits over base body 150 and is held in a forward position by bolts 172, and end cap 154 is threaded into the proximal end of base body 150. End cap 154 contains a channel 156 through which electrical and fluidic connections are made to the instrument port 101, and through which a surgical instrument may be inserted.

FIGS. 4A and 4B show a side view of the instrument port 101 as illustrated in FIG. 3. Certain additional components 176 of the instrument port 101 that are disposed between the base body 150 and collar 170 can be partially seen in FIGS. 4A and 4B. As discussed, a proximal end of distal bulb 120 is pulled against a gasket and port body 110 by connecting rods 130. The connecting rods are disposed parallel to the port body 110.

Figure 4C:
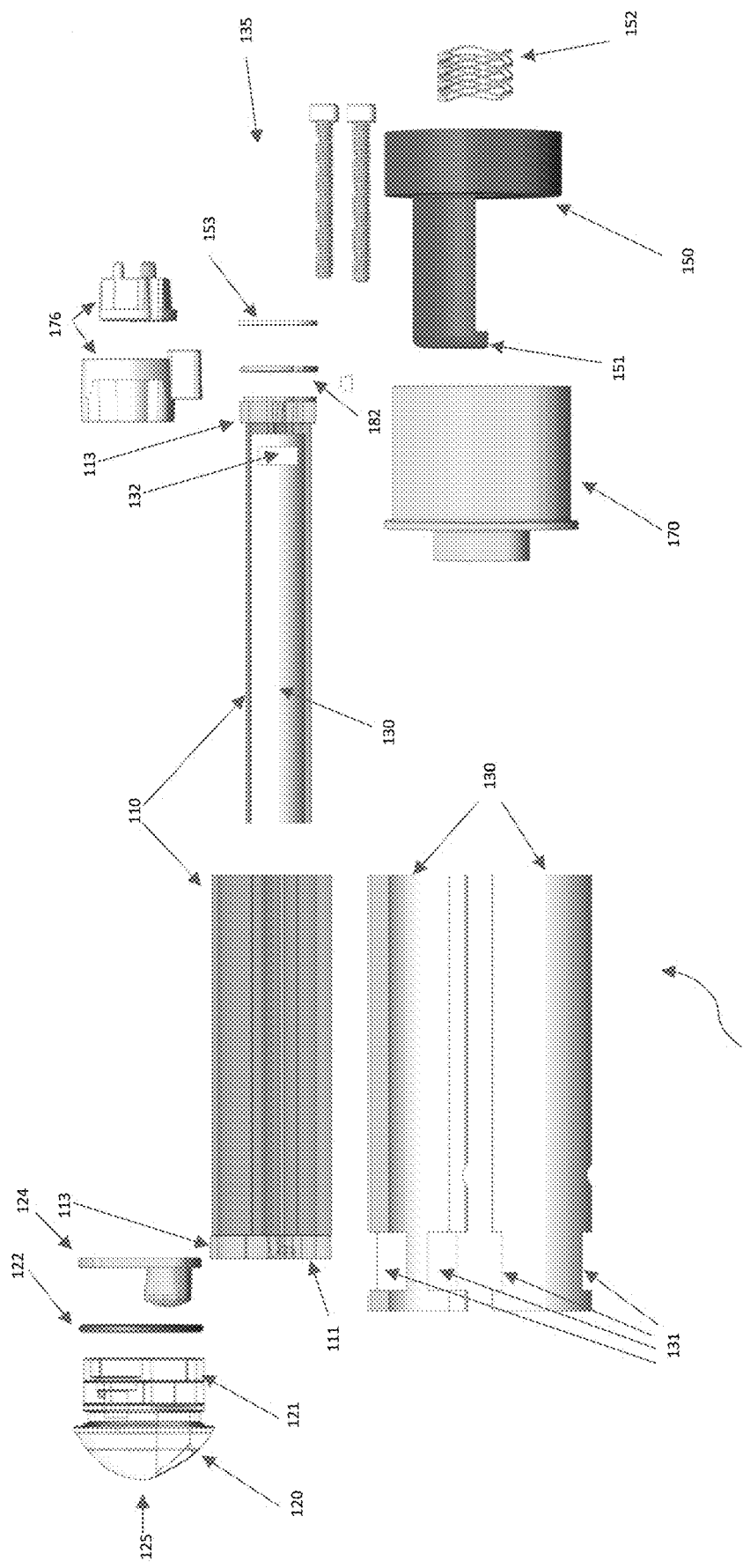
FIG. 4C is an exploded side view, of a portion of a surgical apparatus including the instrument port disclosed herein, according to one more embodiments.

FIG. 4C shows an exploded side view of the instrument port 101 as viewed in FIGS. 4A and 4B. Between bulb 120 and distal end 111 of port body 110 are O-ring seal 122 and valve gasket 124. The O-ring seal 122 seals the bulb 120 to the sleeve 112, and the valve gasket 124 seals the bulb 120 to the port body 110. At proximal end 135 of port body 110, disposed between the proximal end 135 and base body 150, are additional components 176 as well as gasket 182 and washer 153. Washer 153 rests against distal end of spring 152, whose proximal end is adjacent to base cap 154 of FIG. 4A (not shown in FIG. 4C). The port body 110 can optionally include faceplates 113 at its distal end 111 and at its proximal end. The faceplates 113 can be a segment of the port body 110 that includes a different cross-sectional diameter and/or one or more channels that are disposed at an angle (other than 180 degrees) with respect to one or more corresponding channels in the port body 110. The faceplates 113 can be manufactured separately to reduce manufacturing costs and complexity. In other embodiments, the port body 110 can be manufactured to include the faceplate 113 segments as a single integral unit.

The connecting rods 130 are used to mechanically detachably affix the various components of the instrument port 101 to each other, and to maintain sufficient compression against seals and gaskets so as to maintain fluidic integrity of the instrument port 101, even while the instrument port 101 is subject to mechanical stresses during use. It is desirable to maintain a fluid-tight connection between the bulb and the distal end of the port body, which is disposed inside the patient's body during surgical procedures. The connecting rods 130, which function as mechanical tension members, may comprise aluminum, such as cast and/or extruded aluminum. In some embodiments, the connecting rods 130 are extruded and then machined to form notches 131. As shown in FIG. 4C, connecting rods 130 comprise notches 131 at distal end 125; these notches 131 mechanically engage with flanged portion 121 of bulb 120. At proximal end 135, connecting rods 130 comprise notches 132 that mechanically engage with flanged portion 151 of base body 150. Those skilled in the art will appreciate that variations on the present preferred examples may be implemented to suit a given application. For example, mechanical couplings, e.g., flanges, threaded couplings, bayonet style couplings, and similar couplings are also usable in various embodiments. Therefore, where reference (including in the appended claims) is made to a "flange", it should be understood that a mechanical coupling of any suitable nature is meant thereby, including couplings secured to one another by threading, welding, adhesive or other mechanical securement features including rivets, pressure fittings, frictional couplings or others as known to those skilled in the art.

It is noted that connecting rods 130 can mechanically engage with one or more mechanical connection points on the bulb 120 and on the base body 150. The mechanical connection points may be referred to in this disclosure as a flange or flanged portion 121, 151, 1121. The mechanical connection point(s) can include one or more recesses and/or indentations defined in the bulb 120, one or more grooves and/or slots defined in the bulb 120, one or more cavities and/or holes defined in the bulb 120, one or more ridges or raised edges on the bulb 120, or other mechanical connection point. The connecting rods 130 include one or more complementary mechanical connection points, sometimes referred to herein as notches 131, that mechanically engages with the mechanical connection points on the bulb 120. The complementary mechanical connection points can include a notch (e.g., notches 131), a pin or other mechanical extension, a bolt, or other complementary mechanical connection point.

Figure 5A:
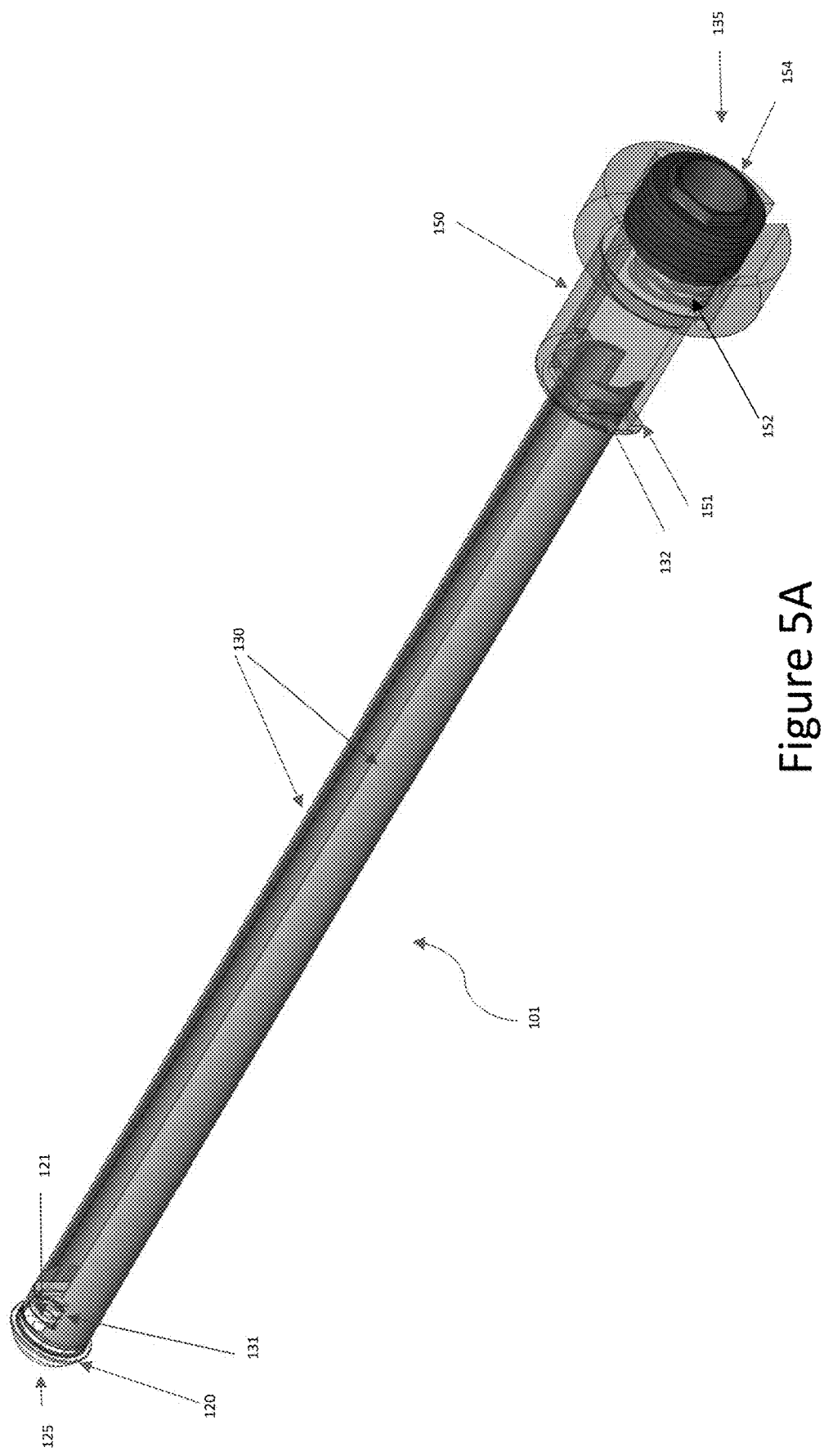
FIGS. 5A and 5B are simplified perspective and side views, respectively, of the instrument port disclosed herein, with certain components not shown in order to illustrate mechanical aspects of the invention, according to one or more embodiments.
Figure 5B:
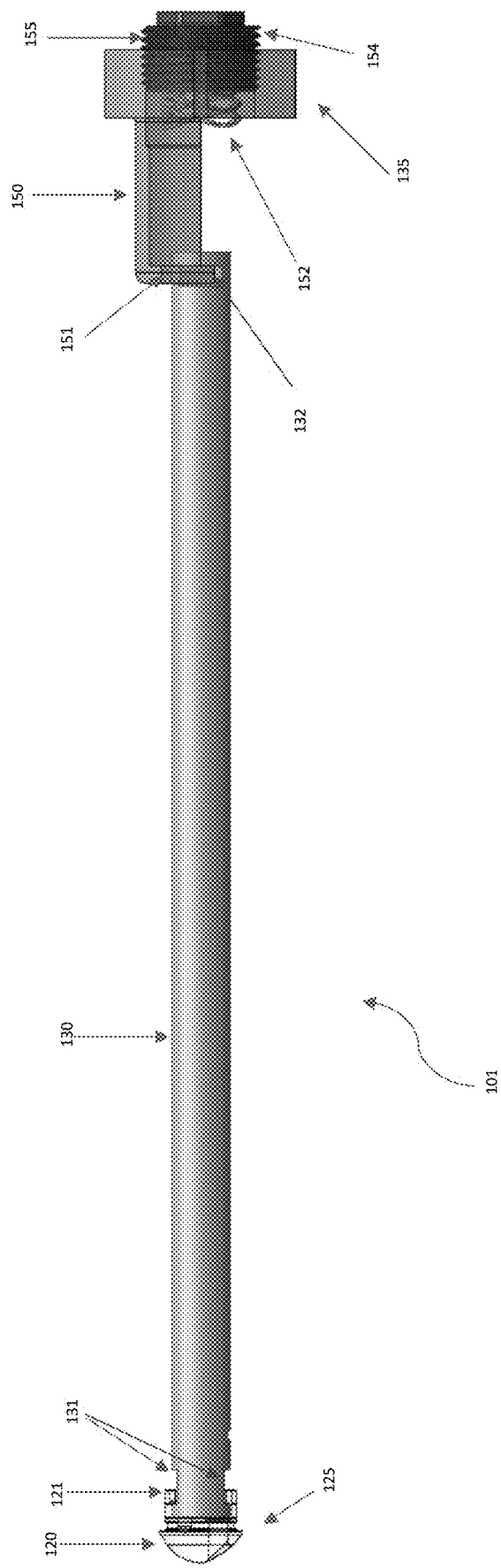

FIGS. 5A and 5B show, in perspective and side views respectively, the mechanical connection between connecting rods 130 and base body 150 and between connecting rods 130 and bulb 120. Other portions of instrument port 101 are not shown in order to better illustrate these mechanical connections. Bulb 120 is at distal end 125 of the apparatus 100, with notches 131 in the distal ends of connecting rods 130 engaged with proximal flanged portion 121 of bulb 120. At the proximal end 135 of the apparatus, base body 150 is shown, partially transparent for illustrative purposes, along with end cap 154 and spring 152; protruding portion 151 of base body 150 is mechanically engaged with notches 132 in connecting rods 130 at their proximal ends. End cap 154 has threads 155 on its lateral surface that mate with threads on the interior surface of an aperture in base body 150, and allows the depth at which end cap 154 is inserted into base body 150 to be adjusted by rotating end cap 154.

FIGS. 6A and 6B show, in side and top views respectively, a part of instrument port 101, according to some embodiments. The instrument port 101 includes a bulb 120 attached thereto at distal end 125 thereof, and a base body 150, end cap 154, and collar 170 at proximal end 135 thereof. In each drawing, notches 131 in connecting rods 130 engage mechanically with flanged portion 121 of bulb 120, as well as with compressible valve gasket 124. In FIG. 6A one connecting rod 130 is seen in the foreground, with the other being obscured from view. In FIG. 6B, two connecting rods 130 can be seen, one on either side, viewed from above.

Figure 7:
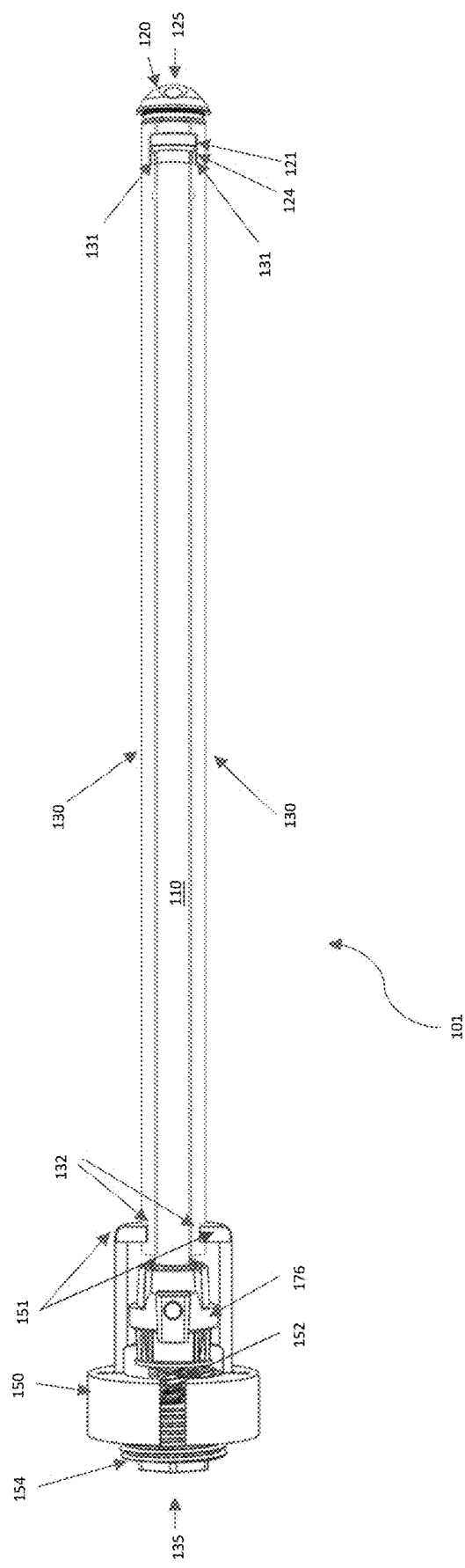
FIG. 7 is a simplified side view of the instrument port disclosed herein, with certain components omitted in order to illustrate internal components, according to one or more embodiments.

FIG. 7 presents a similar view to that of FIG. 6B, in which collar 170 from FIGS. 6A and 6B has been removed, revealing parts at proximal end 135 that were obscured by collar 170 in those figures. Base body 150 comprises a protruding portion 151 at its distal end, which protruding portion 151 mechanically engages with notches 132 near the proximal end of connecting rods 130. The protruding portion 151 can be L-shaped, such as a bracket. End cap 154 is threaded into the proximal end of base body 150, and spring 152 is disposed between end cap 154 and components 176, which in turn are disposed between spring 152 and the proximal end of port body 110.

Connecting rods 130 hold bulb 120 at a fixed position with respect to base body 150. The distance from end cap 154 to bulb 120 can be adjusted by turning end cap 154 to increase or decrease the degree of its insertion into base body 150. Increasing the degree of insertion reduces the space available for spring 152, components 176, port body 110 and compressible gasket 124. Thus, increasing the degree of insertion is effective to take out any slack between these parts, and to increase compression in spring 152 and gasket 124, as well as any other gaskets that may be in the instrument port 101, such as between port body 110 and components 176, or between components 176, or between components 176 and connections to other parts of the instrument port 101. End cap 154 is covered by housing 140 so that the end cap 154 is inaccessible to the surgeon or other user during surgery for safety reasons. For example, the surgeon may accidentally loosen the end cap 154 during surgery, which could breach the seal, formed by the compressible gasket 124, between the port body 110 and the bulb 120.

Figure 8A:
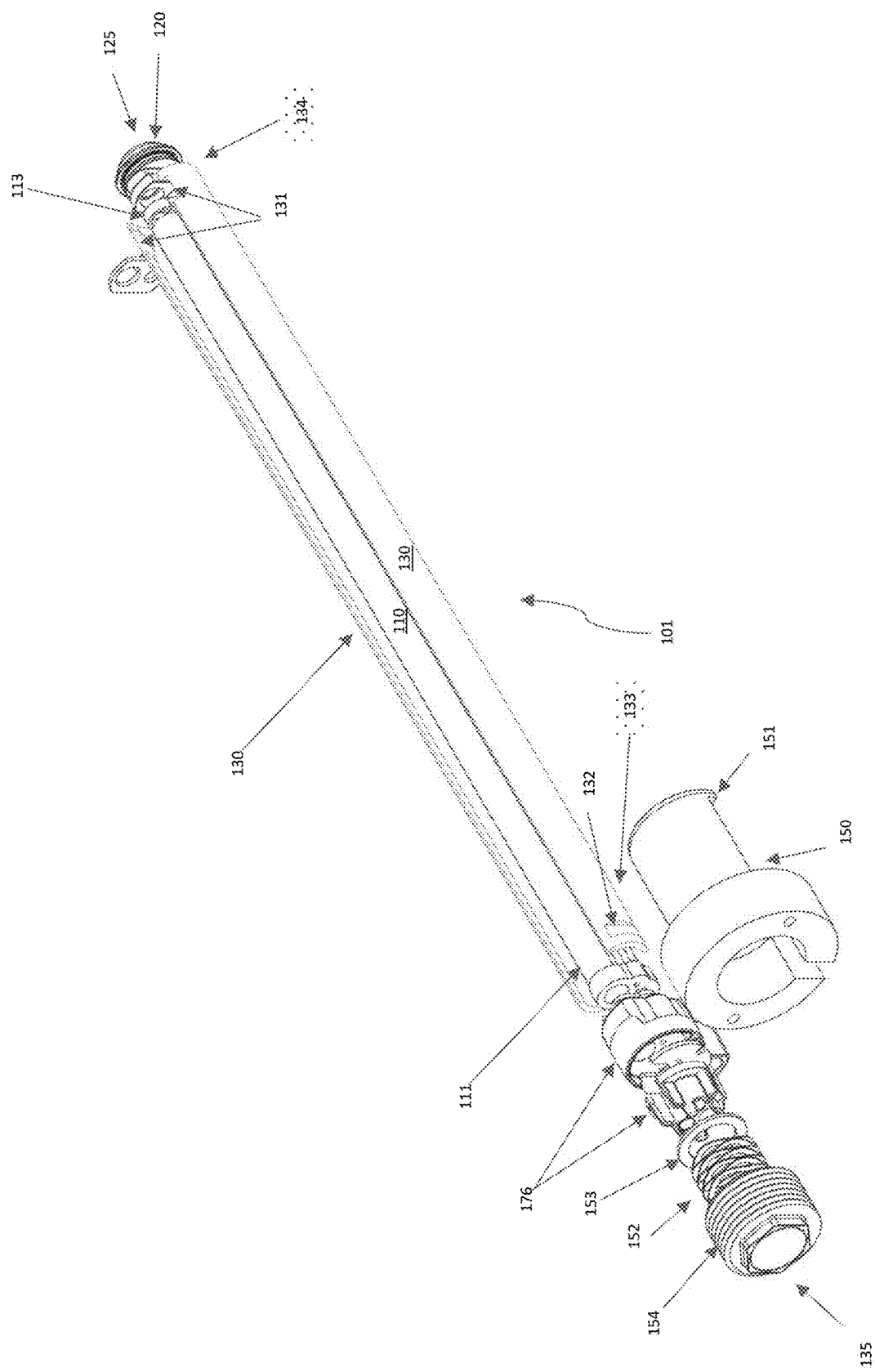
FIG. 8A is an exploded perspective view of the instrument port disclosed herein, according to one or more embodiments.
Figure 8B:
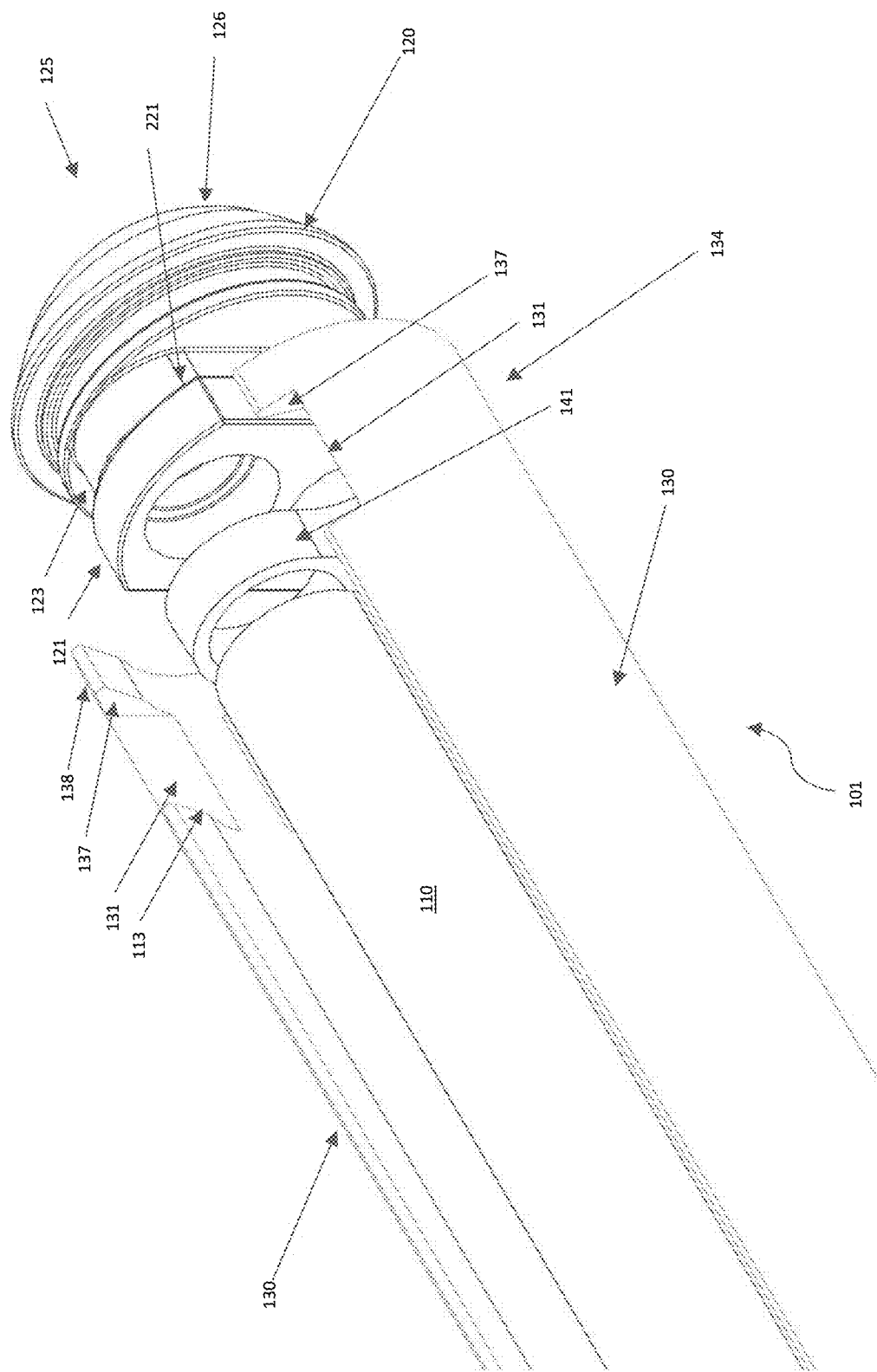
FIG. 8B is an enlarged view of the distal portion of the apparatus illustrated in FIG. 8A.
Figure 8C:
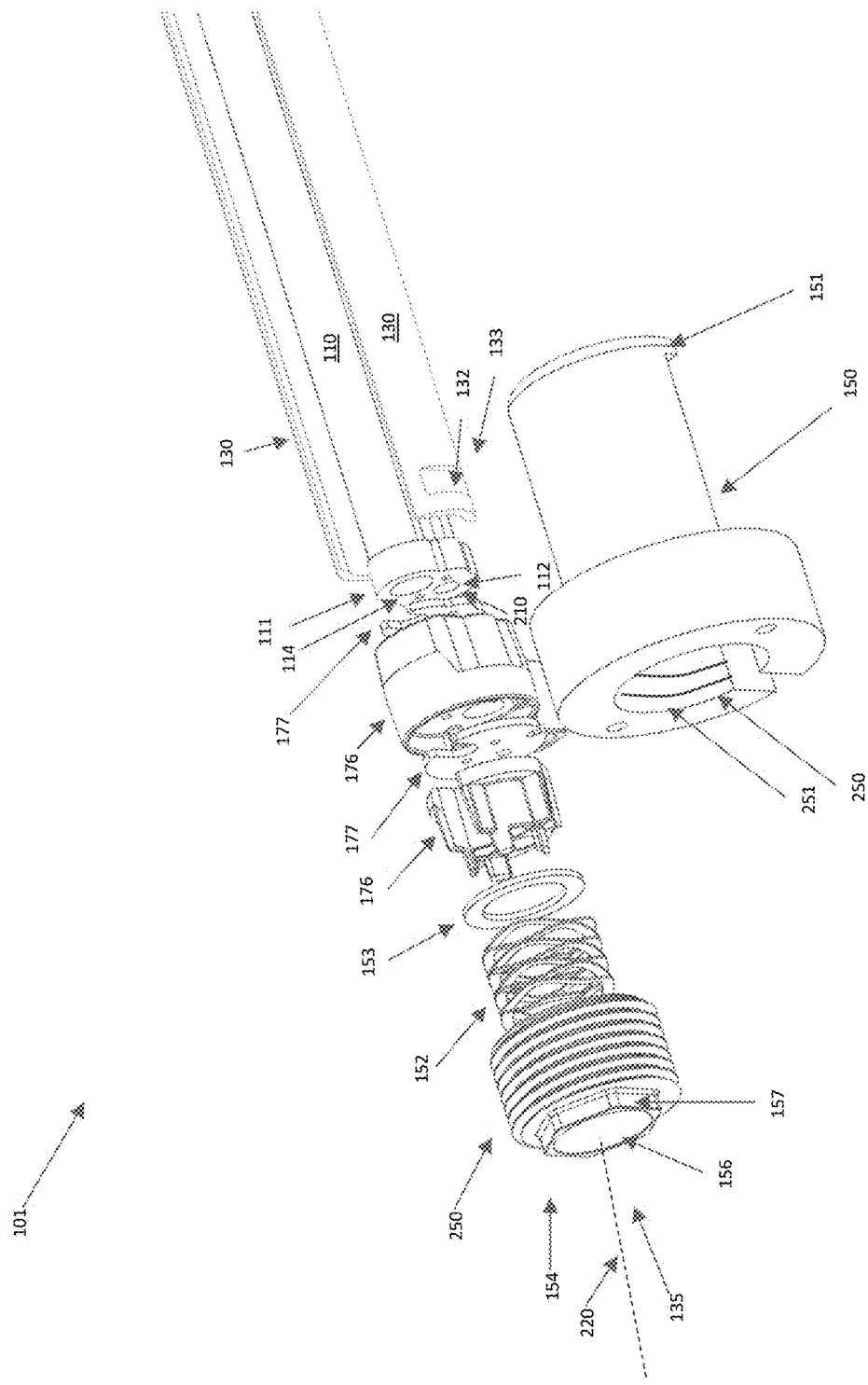
FIG. 8C is an enlarged view of the proximal portion of the apparatus illustrated in FIG. 8A.

FIGS. 8A, 8B and 8C show exploded perspective views of a portion of instrument port 101 according to one or more embodiments. Distal end 125, including bulb 120, are shown in greater detail in FIG. 8B, and proximal end 135, including base body 150 and end cap 154, are shown in greater detail in FIG. 8C. Bulb 120 includes flanged portion 121 at its proximal end, narrowed portion 123 distal to flanged portion 121, and rounded or hemispherical portion 126 at its distal end. Proximal to bulb 120 is port body 110, with distal faceplate 113 disposed between them (gasket 124, disposed between the distal faceplate 113 and bulb 120 is not illustrated in FIG. 8C). As illustrated, port body 110 is cylindrical and/or generally cylindrical, though it can be other shapes.

A plurality of connecting rods 130 are disposed parallel to port body 110. Each connecting rod 130 includes a proximal rod portion 133 and a distal rod portion 134. The distal rod portion 134 includes proximal-facing surface 137. Bulb 120 is configured so that flanged portion 121, along with valve gasket 124 and/or other components, mechanically engage with notches 131, such that a portion of proximal-facing surface 137 of finger or leaf 138 is in contact with a portion of the distal-facing surface 221 of flanged portion 121 of bulb 120, such that the notches 131 can pull the proximal-facing surface 137 towards the valve gasket 124 and port body 110 to form a fluid seal. Connecting rods 130 comprise finger or leaf 138 at their distal ends, distal to notches 131; bulb 120 is configured so that finger or leaf 138 will fit within the space alongside narrowed portion 123 of bulb 120.

FIG. 8C shows proximal end of instrument port 101 of FIG. 8A in greater detail. A portion of port body 110 is shown, including proximal end 111. The port body 110 includes first and second port body interior lumens 112, 114 that extend from the proximal end 111 to the distal end 141 of the port body 110. Connecting rods 130 are alongside and parallel to port body 110. At or near the proximal end of each connecting rod 130 is notch 132, which mechanically mates with protruding portion 151 of base body 150 when the instrument port 101 is assembled, such that a part of a proximal facing surface of such protruding portion 151 is in contact with a part of a distal-facing surface of notch 132, with the surfaces able to exert a mechanical pressure on each other. Thus, the base body 150, connecting rods 130 and bulb 120 are held in place with respect to one another, with respect to motion along a longitudinal axis 220 of the instrument port 101.

End cap 154 encloses the other parts of the instrument port 101 between itself and bulb 120, including spring 152, washer 153, components 176, gaskets 177, port body 110, and compressible gasket 124. End cap 154 is turned to adjust the degree of its insertion into base body 150 (e.g., via respective threads), effecting a tightening or loosening of the space available for the components between end cap 154 and bulb 120, and thus increasing or decreasing the compression in spring 152 and gaskets 177 and 124, which can increase or decrease the mechanical force provided by the spring 152 and the connecting rods 130. Thus, the position (or "tightness") of the end cap 154 with respect to base body 150 corresponds to the magnitude of compression of spring 152. In the compressed state, the spring 152 generates a first spring mechanical force in the proximal direction towards the distal end of the end cap 154, and a second spring mechanical force in the distal direction towards the proximal end 111 of the port body 110. The first and second mechanical forces press the distal end of the port body against gasket 124 (not illustrated in FIG. 8C) and bulb 120, which is held in place by connecting rods 130. Therefore, the first and second mechanical forces cause the distal end of the port body 110, the gasket 124, and the bulb 120 to be compressed to secure the bulb 120 to the port body 110 and to form a fluid-tight seal therebetween.

End cap 154 comprises on its proximal face a raised hex-head with parallel raised surfaces 157 allowing end cap 154 to be turned with an open-end wrench or similar tool. End cap 154 comprises channel 156 extending from its proximal to its distal end, allowing surgical instruments, as well as fluid and electrical conduits, to pass through end cap 154 to and through components 176 and port body 110. One or more pairs of parallel raised surfaces can be disposed on opposing sides of the channel 156. The raised surfaces 157 can be rotated about the longitudinal axis 220 that passes through the channel 156 to tighten or loosen the end cap 154.

Figure 8D:
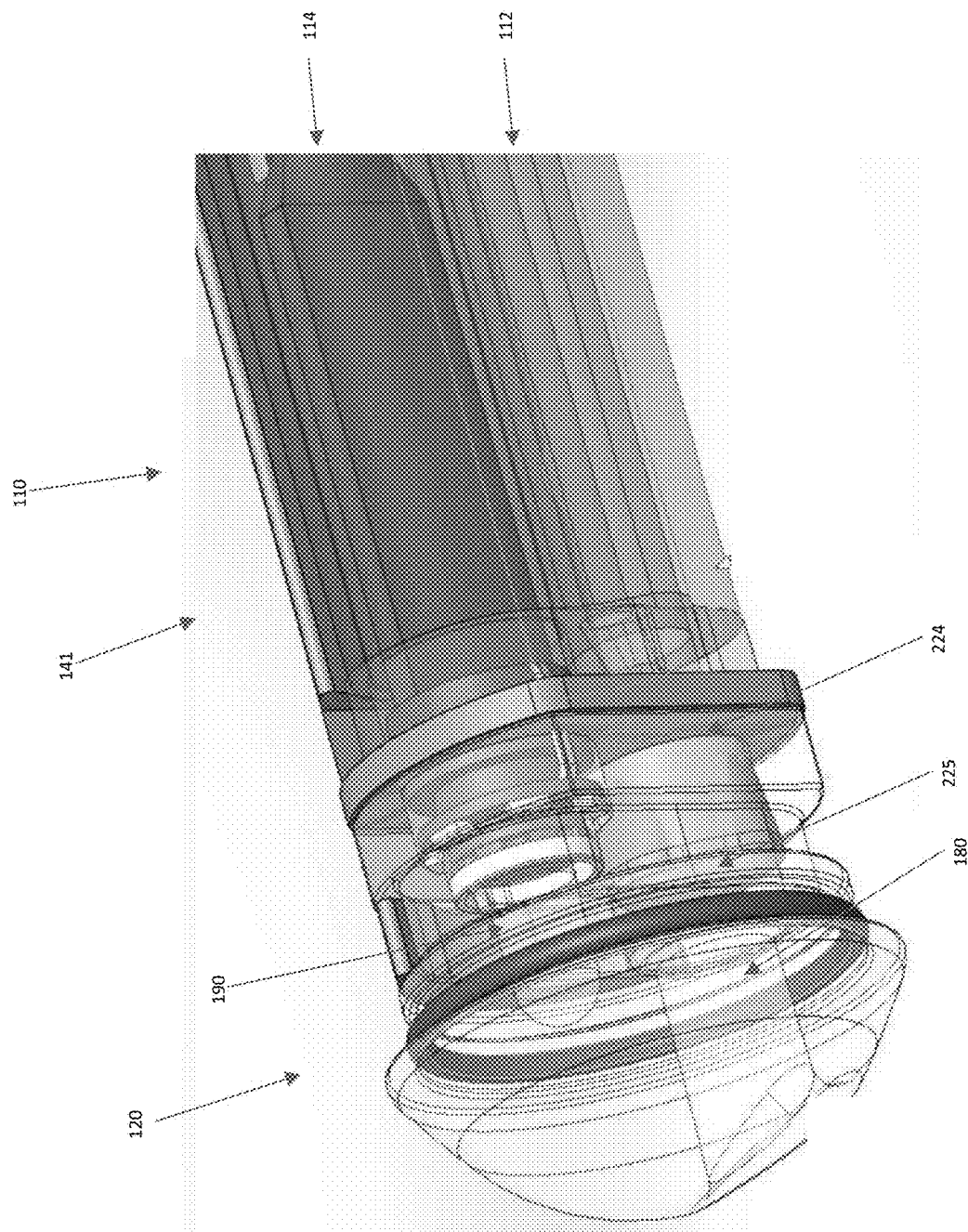
FIG. 8D illustrates a perspective view of the distal end of the port body and the bulb according to one or more embodiments.

FIG. 8D illustrates a perspective view of the distal end 141 of the port body 110 and the bulb 120 according to one or more embodiments. For purpose of illustration, the port body 110 and bulb 120 are shown in a partial-transparent view. As can be seen the first port body lumen 112 is aligned with a first bulb channel 180 to form an instrument channel to receive an instrument. The compressible gasket 124 includes a gasket hole 224 and a valve 225 that are aligned with the first bulb channel 180 and the first body lumen 112. The second port body lumen 114 is aligned with a second bulb channel 190 to form an imaging channel, in which electrical conduits can be disposed to electrically connect to an imaging system disposed in the bulb 120.

As can be seen, a hollow cylindrical body, sometimes referred to as end cap 154, has external threads 254 that mate with internal threads 251 defined in an aperture 250 of the base body 150 to mechanically couple the distal end of the hollow cylindrical body 154 to the proximal end of the base body 150. The hollow cylindrical body 154 has a hollow cylindrical body channel, sometimes referred to as channel 156, that extends from the proximal end to the distal end of the hollow cylindrical body 154. The hollow cylindrical body channel is aligned with the instrument channel (i.e., with first port body lumen 112 and first bulb channel 180).

Each connecting rod 130 includes distal rod portion 134 that is mechanically coupled (e.g., via notch 131) to a respective or corresponding distal-facing exterior surface 221 of bulb flange 121 of bulb 120. Each connecting rod 130 also includes a proximal rod portion 133 that is mechanically coupled (e.g., via notch 132) to a respective proximal-facing surface 210 of the port body 110. Each connecting rod 130 also includes a distal rod portion 134 that is configured to fix the position of the bulb 120 so that the first and second spring mechanical forces can press the port body 110 against the gasket 124 (not illustrated in FIG. 8D) and the bulb 120 to compress these components together and to form a compression seal therebetween. The compression of the bulb 120, the gasket 124, and the port body 110 secures the bulb 120 to the port body 110 and forms a fluid-tight seal therebetween.

Figure 9A:
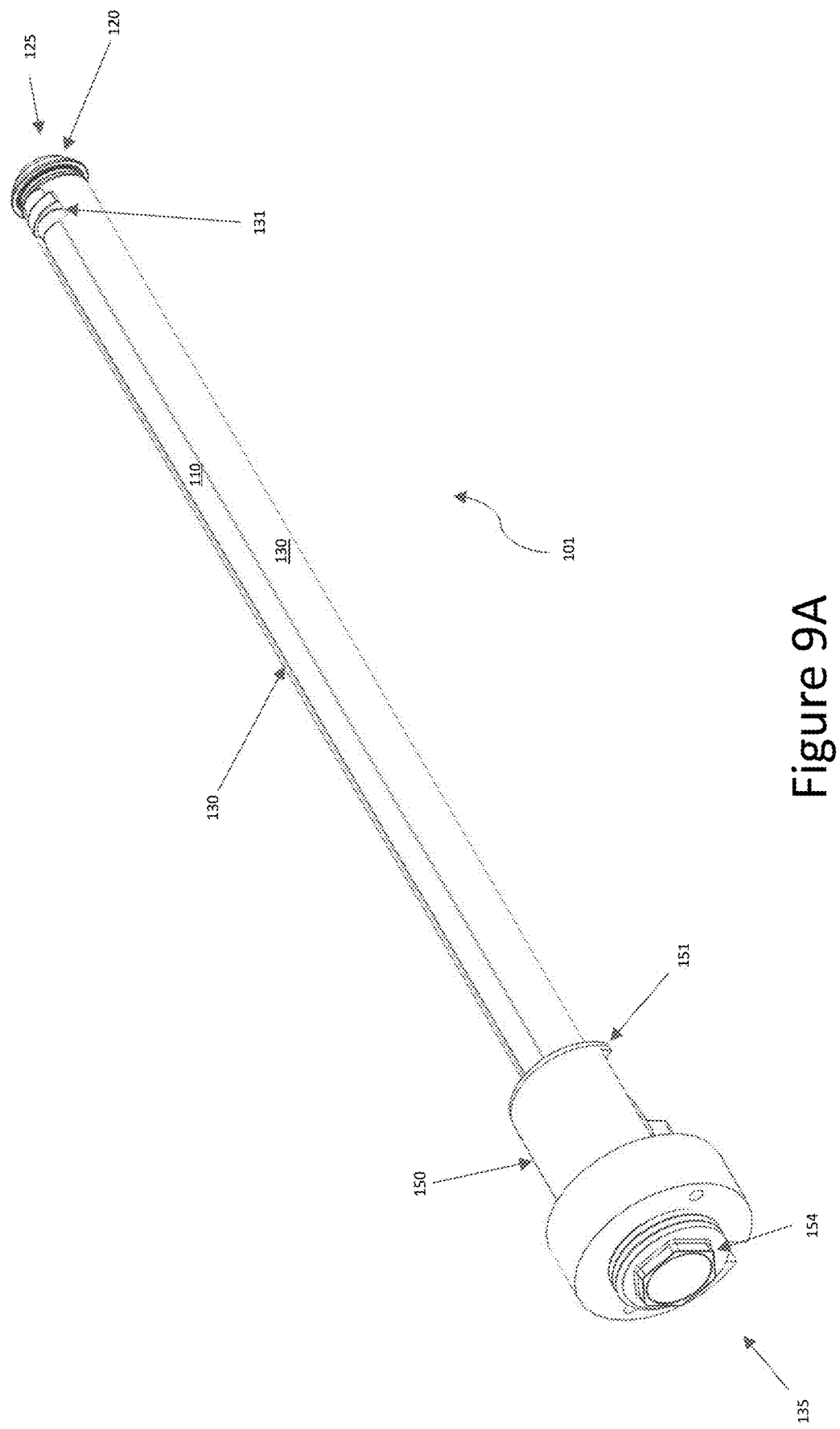
FIGS. 9A and 9B are perspective and bottom views, respectively, of the instrument port disclosed herein, with certain components omitted in order to illustrate mechanical features, according to one or more embodiments.
Figure 9B:
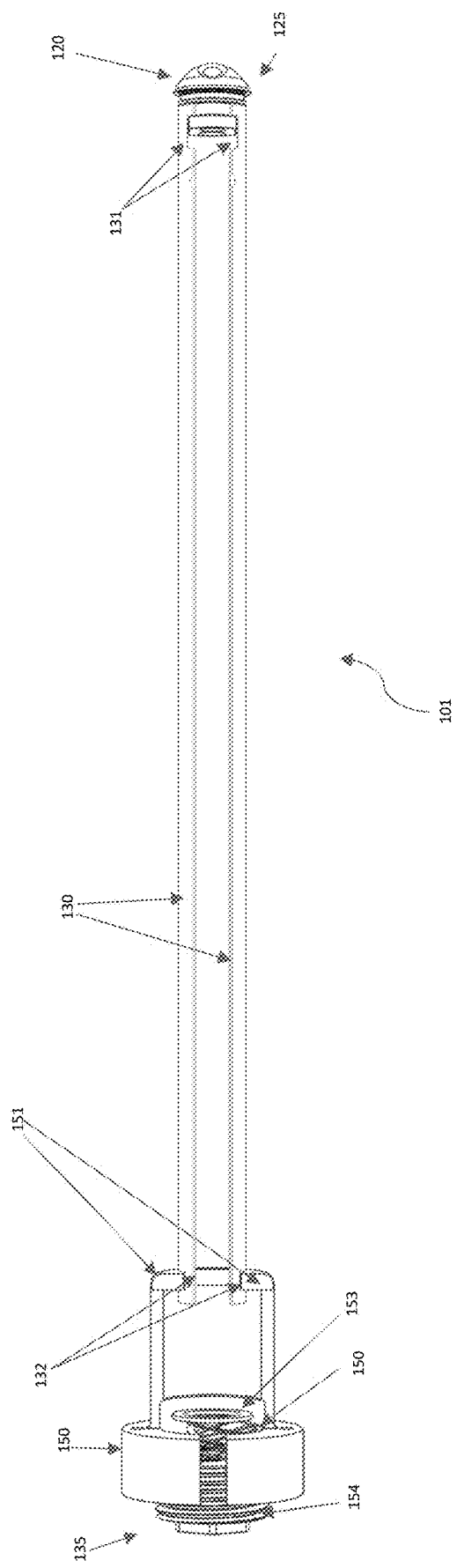
Figure 10:
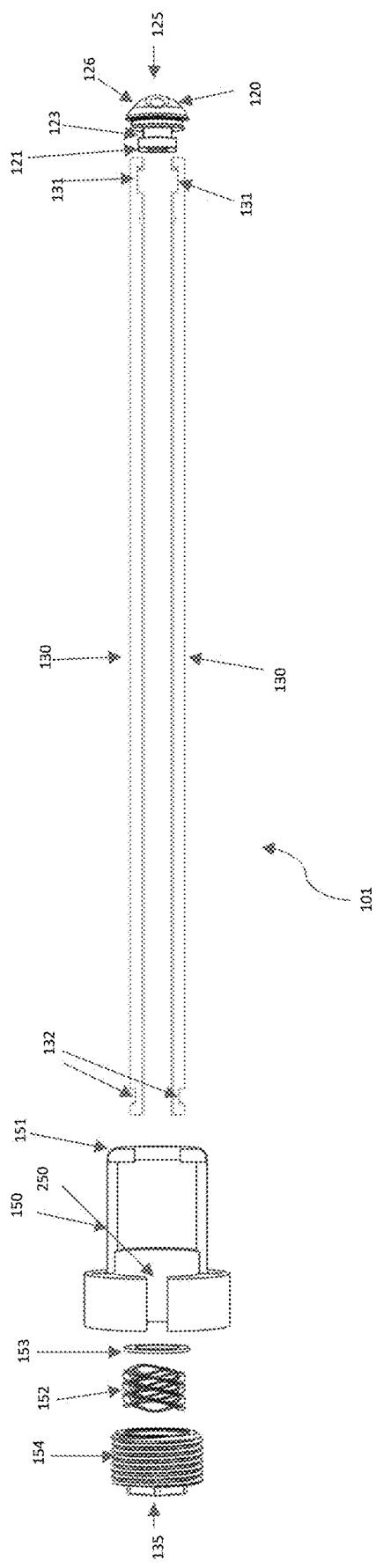
FIG. 10 is an exploded view of the components of the instrument port as depicted in FIG. 9B.

FIGS. 9A and 9B show perspective and side views, respectively, of a portion of instrument port 101 according to one or more embodiments. Distal bulb 120 is at distal end 125 thereof, and base body 150 and end cap are at proximal end 135 thereof. FIG. 10 shows an exploded side view of the instrument port 101 as seen in FIGS. 9A and 9B. Again, bulb 120 can be seen at distal end 125 of the apparatus, with the bulb including flanged portion 121 and narrowed portion 123, for engagement with notches 131 of connecting rods 130. Base body 150 can be seen at proximal end 135 of the apparatus, including protruding portions 151, for engagement with notches 132 of connecting rods 130, and end cap 154 is threaded into internal threads defined in a wall of an aperture 250 in base body 150 so as to enclose and compress the components between end cap 154 and bulb 120, including spring 152.

Figures 11A, 11B:
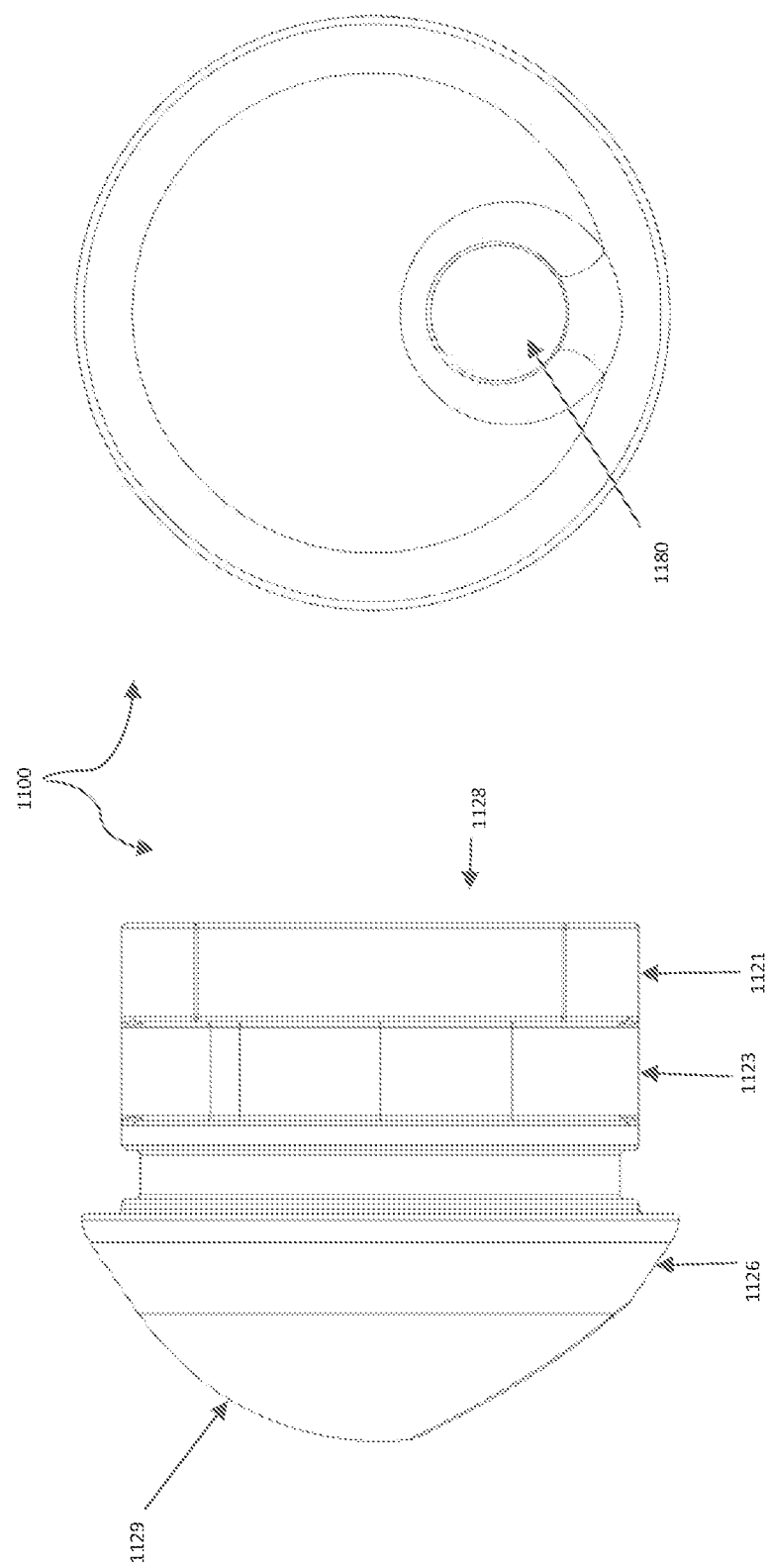

FIGS. 11A-E show various views of a distal tip of a surgical device comprising a bulb, according to one or more embodiments of the invention disclosed herein. Bulb 1100 (which may be the same as or similar to bulb 120 as described herein) is seen in side view in FIG. 11A, in front view (i.e. as viewed from the distal end) in FIG. 11B and in rear view (i.e. as viewed from the proximal end) in FIG. 11C FIGS. 11D and 11E show perspective views, with the proximal face visible in FIG. 11D and the distal face visible in FIG. 11E.

Bulb 1100 comprises rounded distal portion 1126, narrowed central portion 1123 and flanged proximal portion 1121, all rigidly attached to one another and/or comprising a single piece of material and/or comprising the same material. In some embodiments, the single piece of material and/or the same material includes an acrylic thermoplastic. Distal portion 1126 has a rounded, convex exterior distal surface 1129, whose shape may have optical properties. Flanged proximal portion 1121 has a flat proximal exterior surface 1128; other shapes for such proximal exterior surface 1128 may be present in other embodiments. Proximal exterior surface 1128 is configured to mate with a corresponding surface of a valve gasket, which may be the same as or similar to valve gasket 124 of FIG. 4C, or similar component that helps maintain the fluidic isolation and integrity of the different parts of the system of which the bulb 1100 is a part.

Bulb 1100 comprises an instrument channel 1180 extending from its proximal surface 1128 to its distal surface 1129, through which a surgical instrument can pass for use inside the body of a patient, such as in a surgical site. Such an instrument would extend from the proximal end of an instrument port or other surgical apparatus of which bulb 1100 is a part, outside of the patient's body, though a first channel contained in a port body that extends into the patient's body during use. In a typical embodiment, the distal end of the port body and the proximal face 1128 of the bulb would have a valve gasket disposed between them, allowing a surgical instrument to be deployed through an instrument channel in the port body, though a valve in the valve gasket, and through the instrument channel 1180 in the bulb 1100, to reach the relevant tissue or space inside the patient's body.

The bulb 1100 comprises an imaging channel 1190, seen in FIGS. 11C-D, open to the proximal face 1128 and closed to the distal face 1129 of the bulb. Channel 1190 is fluidically isolated from channel 1180. The imaging channel 1190 extends from an aperture 1196 defined in the proximal side or face 1128 and terminates between the proximal and distal sides or faces 1128, 1129 of the bulb 1100. Imaging channel 1190 is fluidically isolated from instrument channel 1180. Imaging channel 1190 is configured to receive and/or retain an imaging system, which may comprise a camera and/or illumination source. The distal portion 1126 of the bulb 1100 is formed of a material that is at least partly optically transparent to one or more wavelengths of light emitted by illumination source 1194, allowing the camera 1193 to capture images of the surgical site, including the patient's bodily tissue and any surgical instruments being used at the site. The illumination source 1194 may comprise one or more light-emitting diodes (LEDs), and may be disposed adjacent to, surrounding, and/or integrated with camera 1193, in any configuration that permits the camera to capture images of the surgical site. In some embodiments the illumination source 1194 may comprise a light guide and a source of illumination located elsewhere within or exterior to a surgical apparatus of which distal bulb 1100 is a part, by which light is conveyed from such exterior source to bulb 1100.

Imaging channel 1190 is open to the proximal face 1128 of the bulb, allowing electrical connection to be made to the camera 1193 and/or illumination source 1194, in order to provide power and control signals, and in some embodiments light from an exterior source, to and receive transmitted images from the imaging system 1192. In a typical embodiment, such electrical connections pass through an opening in a valve gasket to a channel in a port body, separate from the instrument channel in such port body, to reach power sources and other circuitry used with the imaging system 1192. The gasket between the port body and the bulb 1100 helps keep the imaging system 1192 fluidically isolated from the surgical site, thus avoiding electrical shorts and other malfunctions from contact of electrical equipment and connections with bodily or other fluids, and also avoiding the possibility of electrical signals being transmitted into the surgical site from the imaging system and causing unintended electrical stimulation of bodily tissue, which could be particularly dangerous during cardiac procedures. Fluidically isolating the imaging system 1192 also reduces the risk of infection during surgery by reducing the number of components exposed to the surgical site. In order for the gasket to form a good seal, the bulb 1100 is compressed against the gasket and the distal end of the port body. The connecting rods press on the distal-facing surface 1127 of the flanged proximal portion 1121 of the bulb 1100 while a spring presses against a proximal end of the port body to press the distal end of the port body against the gasket and the bulb to form a tight seal and to secure the bulb 1100 to the port body. A tight seal is particularly necessary to maintain the integrity of the seal when the surgical apparatus is subject to stresses, including bending stresses, during use while it is being manipulated by the surgeon inside the body of the patient, particularly when encountering hard or stiff bodily tissues of the patient.

FIG. 12 shows a rear/proximal view of an exemplary bulb 1100, which may be the same as or similar to the bulb shown in FIGS. 11A-E, in greater detail, pointing out certain optical features of the bulb. FIG. 13 shows a top view of an exemplary bulb 1100, which may be the same as or similar to the bulb shown in FIGS. 11A-E, with certain optical features and exemplary dimensions shown. Note that the interior surfaces of both lumens, i.e. instrument channel 1180 and imaging system channel 1190, are optical surfaces, as is the exterior distal surface 1129 of the bulb 1100. Light from the illumination source 1192 passes through these surfaces and is refracted on the way to the site being imaged, and the light reflected from the site being imaged is refracted through these surfaces on the way to the camera 1193 where such light is captured as an image.

The apparatus with instrument ports and distal bulb tip described herein can be used to perform cardiac procedures, such as beating heart cardiac procedures. Examples of cardiac procedures that can be carried out by the instrument ports described herein include closure of heart defects, such as septal defects, heart valve annuloplasty, and other procedures. The imaging capabilities provided by the instrument ports described here provide high quality imaging of the surgical procedure, thereby enabling complex surgical procedures to be carried out with a high degree of precision.

In the foregoing specification, certain aspects have been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

What is claimed is:

1. An instrument port for introducing a surgical instrument into a surgical site inside a body of a patient, the instrument port comprising:
   a port body having a port body interior lumen extending from a proximal end of the port body to a distal end of the port body;
   a bulb disposed at the distal end of the port body, the bulb comprising a bulb flange at a proximal end of the bulb, the bulb further comprising a bulb channel extending from the proximal end of the bulb to a distal end of the bulb, the bulb channel aligned with the port body interior lumen to form an instrument channel to receive the surgical instrument;
   a base body disposed at the proximal end of the port body, said base body having an aperture extending from a proximal end of the base body to a distal end of the base body, wherein internal threads are defined in the proximal end of the base body, the proximal end of the base body defining a proximal portion of said aperture;
   a hollow cylindrical body having external threads that mate with the internal threads of the base body, the hollow cylindrical body having a hollow cylindrical body channel extending from a proximal end of the hollow cylindrical body to a distal end of the hollow cylindrical body, the hollow cylindrical body channel aligned with the instrument channel, wherein the distal end of the hollow cylindrical body is mechanically coupled to the proximal end of the base body; and
   a plurality of connecting rods disposed parallel to the port body, each connecting rod comprising a distal rod portion that is mechanically coupled to a respective distal-facing surface of the bulb flange, each said connecting rod further comprising a proximal rod portion that is mechanically coupled to a respective proximal-facing surface of the base body,
   wherein tension in the plurality of connecting rods maintains compression between the bulb flange and the base body.

2. The instrument port of claim 1, further comprising a spring disposed between the distal end of the hollow cylindrical body and the proximal end of the port body, wherein a compression of the spring causes the spring to generate a first spring mechanical force in a proximal direction and a second spring mechanical force in a distal direction, the first and second spring mechanical forces mechanically pressing the port body against the bulb.

3. The instrument port of claim 2, wherein a position of the hollow cylindrical body with respect to the base body corresponds to the compression of the spring.

4. The instrument port of claim 3, wherein moving the position of the hollow cylindrical body in the distal direction increases a magnitude of the first spring mechanical force and the second spring mechanical force.

5. The instrument port of claim 3, wherein moving the position of the hollow cylindrical body in the proximal direction decreases a magnitude of the first spring mechanical force and the second spring mechanical force.

6. The instrument port of claim 2, wherein the first spring mechanical force and the second spring mechanical force compress the port body and the bulb.

7. The instrument port of claim 1, further comprising a compressible gasket disposed between the proximal end of the bulb and the distal end of the port body.

8. The instrument port of claim 7, wherein a spring force pushes the distal end of the port body against the compressible gasket and the bulb to form a fluid-tight seal.

9. The instrument port of claim 7, wherein the compressible gasket includes a gasket hole, the gasket hole aligned with the bulb channel and the port body interior lumen.

10. The instrument port of claim 1, wherein said bulb comprises an imaging system, said imaging system comprising an illumination source and a camera, said camera configured to capture images of the surgical site.

11. The instrument port of claim 10, wherein said port body comprises a second interior lumen, said second interior lumen comprising electrical conduits that are electrically connected to the imaging system.

12. The instrument port of claim 1, wherein the port body has a cylindrical shape.

13. The instrument port of claim 1, wherein the hollow cylindrical body comprises, on the proximal end thereof, one or more pairs of raised surfaces disposed on opposing sides of the hollow cylindrical body channel, said raised surfaces configured to allow the hollow cylindrical body to be rotated about a longitudinal axis that passes through said hollow cylindrical body channel.

14. The instrument port of claim 1, further comprising a housing surrounding the base body and a proximal portion of the port body, said housing comprising a grip by which a surgeon is able to hold and manipulate the instrument port from outside the body of the patient.

15. The instrument port of claim 14, further comprising a sleeve extending from the housing to the distal end of the port body, said sleeve comprising a tube and being disposed outside of and enclosing the port body and the plurality of connecting rods.

16. The instrument port of claim 1, wherein the distal rod portion of each connecting rod includes a notch that engages the respective distal-facing surface of the bulb flange.

17. The instrument port of claim 1, wherein the proximal rod portion of each connecting rod includes a notch that engages the respective proximal-facing surface of the base body.

18. The instrument port of claim 1, wherein the plurality of connecting rods comprise aluminum.

19. The instrument port of claim 1, wherein the proximal rod portion of each connecting rod is configured to exert a mechanical pressure on the respective proximal-facing surface of the base body.

20. The instrument port of claim 1, wherein the plurality of connecting rods have curved profiles.

\* \* \* \* \*

UNITED STATES PATENT AND TRADEMARK OFFICE
CERTIFICATE OF CORRECTION

| | | |
|---|---|---|
| PATENT NO. | : 11,324,555 B2 | |
| APPLICATION NO. | : 15/916667 | |
| DATED | : May 10, 2022 | |
| INVENTOR(S) | : Anthony Maiorano and Jeffrey C. Cerier | |

It is certified that error appears in the above-identified patent and that said Letters Patent is hereby corrected as shown below:

In the Specification

Column 1, Lines 6-9, delete "with U.S. government support under Grant No. 5R42HL132655, awarded by the Heart, Lung, and Blood Institute (NHLBI) of the National Institutes of Health (NIH). The U.S. government has" and insert -- with government support under Grant Number HL132655, awarded by the National Institutes of Health. The Government has --.

Signed and Sealed this
Twenty-eighth Day of November, 2023

Katherine Kelly Vidal
*Director of the United States Patent and Trademark Office*